US008431521B2

(12) United States Patent
Krantz et al.

(10) Patent No.: US 8,431,521 B2
(45) Date of Patent: Apr. 30, 2013

(54) SITE-SPECIFIC CHEMICAL MODIFICATION OF PROTEINS AT THEIR N-TERMINI, ENABLING THE FORMATION OF HOMOGENEOUS ADDUCTS

(75) Inventors: Alexander Krantz, Boston, MA (US); Peng Yu, Malden, MA (US)

(73) Assignee: Advanced Proteome Therapeutics, Inc., Boston, MA (US)

( * ) Notice: Subject to any disclaimer, the term of this patent is extended or adjusted under 35 U.S.C. 154(b) by 461 days.

(21) Appl. No.: 12/573,860

(22) Filed: Oct. 5, 2009

(65) Prior Publication Data

US 2010/0099649 A1    Apr. 22, 2010

Related U.S. Application Data

(60) Provisional application No. 61/195,132, filed on Oct. 3, 2008, provisional application No. 61/228,365, filed on Jul. 24, 2009, provisional application No. 61/228,349, filed on Jul. 24, 2009.

(51) Int. Cl.
*A61K 38/00* (2006.01)
(52) U.S. Cl.
USPC ............................................. 514/1.1
(58) Field of Classification Search .............. None
See application file for complete search history.

(56) References Cited

FOREIGN PATENT DOCUMENTS

| WO | WO 00/73332 A1 | 7/2000 |
|---|---|---|
| WO | WO 02/067857 A2 | 9/2002 |
| WO | WO 2005/014620 A1 | 2/2005 |
| WO | WO 2008083346 A1 * | 7/2008 |

OTHER PUBLICATIONS

Gilmore et al., Angew. Chem. Int. Ed. 2006, 45, p. 5307-5311.*
Francis et al., ACS Chemical Biology, 2007, vol. 2, No. 4, p. 247-251.*
Tait et al., J Nucl Med, 2006, 47, p. 1546-1553.*
Scheck et al., "Regioselective Labeling of Antibodies through N-Terminal Transamination" ACS Chemical Biology, 2007, vol. 2, pp. 247-251.
Sasaki et al., "N-terminal Labeling of Proteins by the Pictet-Spengler Reaction" Bioorganic & Medicinal Chemistry Letters, 2008, vol. 18, pp. 4550-4553.
Schellenberger et al., "Annexin V-CLIO: A Nanoparticle for Detecting Apoptosis by MRI" Molecular Imaging, 2002, vol. 1, pp. 102-107.
Flavell et al., "Site-Specific 18F-Labeling of the Protein Hormone Leptin Using a General Two-Step Ligation Procedure" Journal of the American Chemical Society, 2008, vol. 130, pp. 9106-9112.
Extended European Search Report for 09818629.9, dated Dec. 10, 2012.

* cited by examiner

*Primary Examiner* — Marcela M Cordero Garcia
*Assistant Examiner* — Kaipeen Yang
(74) *Attorney, Agent, or Firm* — Lathrop & Gage LLP; Brian C. Trinque, Esq.; Andrew T. Wilkins, Esq.

(57) ABSTRACT

Site-specific modifications of proteins at their N-termini are provided. In particular, a chemical modification of proteins at their N-termini via a transamination reaction to form homogeneous adducts such as, the corresponding oxime derivatives is provided. Methods of making and using the adducts in radio-labeling, molecular imaging applications, and treatment of disorders such as cancer, Crohn's disease, arthritis, atherothrombosis and plaque rupture are also provided.

3 Claims, 3 Drawing Sheets

SITE-SPECIFIC CHEMICAL MODIFICATION OF PROTEINS AT THEIR N-TERMINI, ENABLING THE FORMATION OF HOMOGENEOUS ADDUCTS

RELATED APPLICATIONS

This application claims priority to U.S. Provisional Application No. 61/195,132, filed Oct. 3, 2008, titled "Site-Specific Chemical Modification of Annexin Proteins at their N-Termini, Enabling the Formation of Homogeneous Adducts;" U.S. Provisional Application No. 61/228,365, filed Jul. 24, 2009, titled "Site-Specific N-Terminus Modification of Proteins;" U.S. Provisional Application No. 61/228,349, filed Jul. 24, 2009, titled "Swift Linkage Multivalent Technology;" all of which are incorporated herein by reference in their entirety. Additionally, the contents of any patents, patent applications, and references cited throughout this specification are hereby incorporated by reference in their entireties.

FIELD OF THE INVENTION

The present invention generally relates to site-specific modifications of proteins at their N-termini or at sites incorporating carbonyl moieties, enabling the formation of homogeneous protein conjugates. In particular, the present invention relates to chemical modification of proteins at their N-termini via a transamination reaction to form homogeneous adducts such as the corresponding oxime derivatives. The present invention further relates to methods of making and using the adducts in microarrays, the production of fine chemicals and kits, radio-labeling, molecular and optical imaging applications, and the diagnosis and treatment of disorders such as cancer, Crohn's disease, atherothrombosis, arthritis, and plaque rupture.

BACKGROUND

N-terminal modification of certain proteins using transamination reactions has been reported. See for example, Dixon, N-Terminal Modification of Proteins A Review, Journal of Protein Chemistry, 1984, 3, 99-108, and references therein. Dixon reports that the transamination reaction occurs at a pH range of 5-7, is specific for N-terminal amines of α-amino groups and can be used for removal of N-terminal residues of proteins under non-denaturing conditions. See, Improved Conditions for the Removal of 2-oxacyl groups form the N-terminus of proteins, M. Sunde, M. J. Sparkes, and H. B. F. Dixon, Biochim. Biophys. Acta 1998, 1388, 45-52. Other reports of converting human growth hormones to the corresponding terminal keto amides have been reported. See O. Nishimura et al., An efficient chemical method for removing N-terminal extra methionine from recombinant methioylated human growth hormone, Chem. Commun. 1998, 1135-1136. Additional work by Gilmore et al., Angew. Chem. Int. Ed. 2006, 45, 5307-5311 and Christman et al. J. Mat. Chem. 2007, 17 2021-1627 using pyridoxal phosphate shows the oxidation of the N-terminal of select proteins.

However, these methods have a variety of drawbacks. For example, the methods employ harsh reaction conditions under which it is difficult to maintain the folded structure of proteins necessary for their activity. The methods lack the site-specificity and therefore it is difficult to control or limit the reaction to the N-terminal of the proteins. The methods are not generally applicable to a variety of proteins but only work with a selected number of proteins thereby severely limiting the scope of these methods.

Therefore, there remains a need for methods for modifications of proteins that are tolerable, site-specific and can be applied to a variety of proteins. There also exists a need to utilize the resulting adducts of such modified proteins for screening and/or therapy of disorders such as cancer, Crohn's disease, arthritis, atherothrombosis and plaque rupture.

SUMMARY OF THE INVENTION

The present invention generally provides site-specific modifications of proteins. Examples of such proteins include, granulocyte macrophage colony-stimulating factor, human superoxide dismutase, annexin proteins, leptin, myoglobin, albumin, avidin, and an enzyme or antibody. In particular, the present invention provides chemical modification of proteins, e.g. annexin proteins, at their N-termini via transamination reactions which mediate the formation of homogeneous adducts which are derived from bifunctional entities such as bis-alkoxyl amines capable of installing biologically useful ligands or latent reactive groups on protein frameworks. The present invention further provides methods of making and using the adducts in microarrays, the production of fine chemicals and kits, radio-labelling, molecular and optical imaging applications, fusion protein synthesis, and the diagnosis and treatment of disorders such as cancer, Crohn's disease, arthritis, atherothrombosis and plaque rupture.

In one aspect, the invention provides a compound of the formula I:

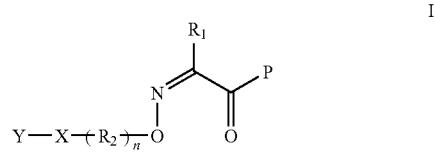

and any isomers thereof, wherein,

P is selected from the group consisting of granulocyte macrophage colony-stimulating factor, human superoxide dismutase, annexin proteins, leptin, myoglobin, albumin, biotin, avidin, and an enzyme or an antibody, $R_1$ is selected from the group consisting of hydrogen, methyl and α-amino acid side chain, $R_2$ is independently selected from the group consisting of optionally substituted $C_1$-$C_{20}$ alkyl, $C_2$-$C_{20}$ alkenyl, and $C_2$-$C_{20}$ alkynyl, X is selected from the group consisting of a covalent bond, O, NR, CO, and NRCO, Y is selected from the group consisting of $OR_3$, $NR_3R_3$, $N(R_3)NR_3R_3$, and $N{=}CR_3Z$, R is selected from the group consisting of hydrogen, $C_1$-$C_{20}$ alkyl, $C_2$-$C_{20}$ alkenyl, $C_2$-$C_{20}$ alkynyl, aryl, cycloalkyl, and heterocycloalkyl, Z is selected from the group consisting of $R_5$—$R_4$—$R_3$, and optionally substituted aryl, $R_3$ is selected from the group consisting of hydrogen, $C_1$-$C_{20}$ alkyl, $C_2$-$C_{20}$ alkenyl, and $C_2$-$C_{20}$ alkynyl, $R_4$ is selected from the group consisting of a covalent bond, O, NR, CO, and NRCO, $R_5$ is selected from the group consisting of $OR_6$, $NR_6R_6$, $N(R_6)NR_6R_6$, and $N{=}CR_6R_6$, $R_6$ is independently selected from the group consisting of hydrogen, $C_1$-$C_{20}$ alkyl, $C_2$-$C_{20}$ alkenyl, and $C_2$-$C_{20}$ alkynyl, n is 1-21, and each optional substitution is selected from the group consisting of optionally radioactive F, Cl, Br, I, OR, SR, COR, NRR, OAr, and NHAr.

In another aspect, the invention provides a compound of the formula II:

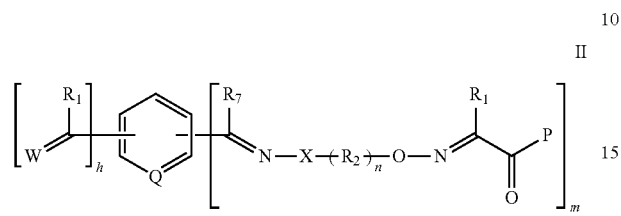

and any isomers thereof, wherein,

P is selected from the group consisting of granulocyte macrophage colony-stimulating factor, human superoxide dismutase, annexin proteins, leptin, myoglobin, albumin, avidin, and an enzyme or antibody, $R_1$ is independently selected from the group consisting of hydrogen, methyl and an α-amino acid side chain, $R_2$ is independently selected from the group consisting of optionally substituted $C_1$-$C_{20}$ alkyl, $C_2$-$C_{20}$ alkenyl, and $C_2$-$C_{20}$ alkynyl, X is selected from the group consisting of a covalent bond, O, NR, CO, and NRCO, W is selected from the group consisting of O, $NOR_3$, $NOR_3N(R_3ONR_3)_2$ and $N=CR_3Z$, Q is CH or N, R is selected from the group consisting of hydrogen, $C_1$-$C_{20}$ alkyl, $C_2$-$C_{20}$ alkenyl, $C_2$-$C_{20}$ alkynyl, aryl, cycloalkyl, and heterocycloalkyl, Z is selected from the group consisting of $R_5$—$R_4$—$R_3$, and optionally substituted aryl, $R_3$ is selected from the group consisting of hydrogen, $C_1$-$C_{20}$ alkyl, $C_2$-$C_{20}$ alkenyl, and $C_2$-$C_{20}$ alkynyl, $R_4$ is selected from the group consisting of a covalent bond, O, NR, CO, and NRCO, $R_5$ is selected from the group consisting of $OR_6$, $NR_6R_6$, $N(R_6)NR_6R_6$, and $N=CR_6R_6$, $R_6$ is independently selected from the group consisting of hydrogen, $C_1$-$C_{20}$ alkyl, $C_2$-$C_{20}$ alkenyl, and $C_2$-$C_{20}$ alkynyl, $R_7$ is hydrogen or methyl, n is 1-21, m is 0-3, h is 0-3 provided that at least one m or at least one h is 1, and each optional substitution is selected from the group consisting of optionally radioactive F, Cl, Br, I, OR, COR, NRR, OAr, and NHAr.

In various embodiments, the invention includes compounds where $R_1$ is hydrogen or methyl. In some embodiments, $R_2$ is $CH_2$. In certain embodiments, X is O. In various embodiments, R is hydrogen, or $C_1$-$C_{20}$ alkyl. In some embodiments, $R_3$ is hydrogen or methyl. In various embodiments, Z is optionally substituted aryl. In certain embodiments, n is 3-14, and m is 1-3. In some embodiments, n is 6. In various embodiments, the invention includes compounds where X is O and Y is $NR_3R_3$, X is NR and Y is $NR_3R_3$, X is NRCO and Y is $N(R_3)NR_3R_3$. In certain embodiments, Z is $R_5$—$R_4$—$R_3$, where $R_3$ is $C_1$-$C_{20}$ alkyl, $R_4$ is CO, and $R_5$ is $OR_6$, where $R_6$ is hydrogen.

In some embodiments, the compound is further substituted with a reduced oxime linkage where at least one oxime linkage is reduced to a corresponding aminoxy group. In certain embodiments, the compound is selected from the group consisting of:

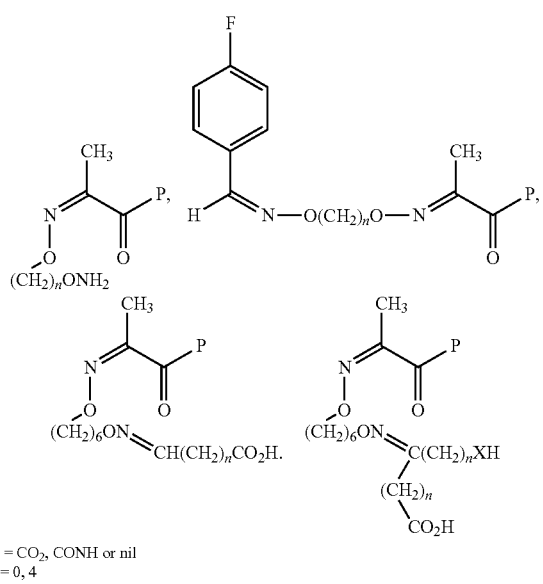

$X = CO_2$, CONH or nil
$n = 0, 4$

In certain embodiments, the compound is selected from the group consisting of:

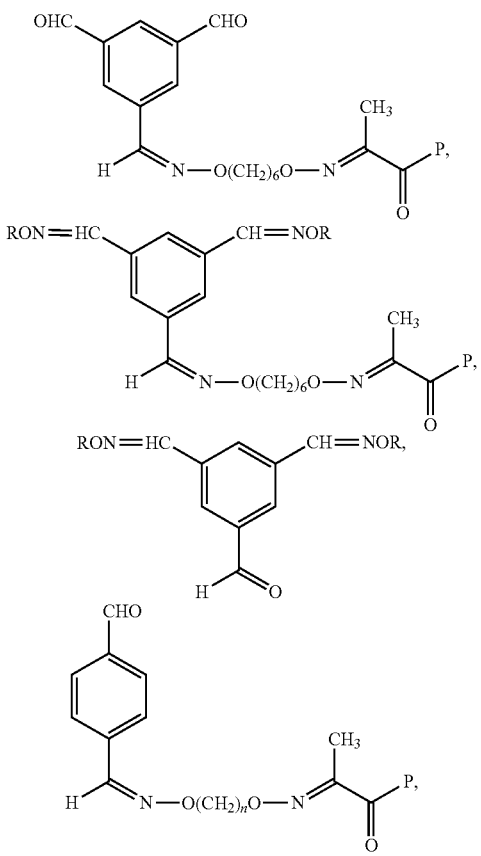

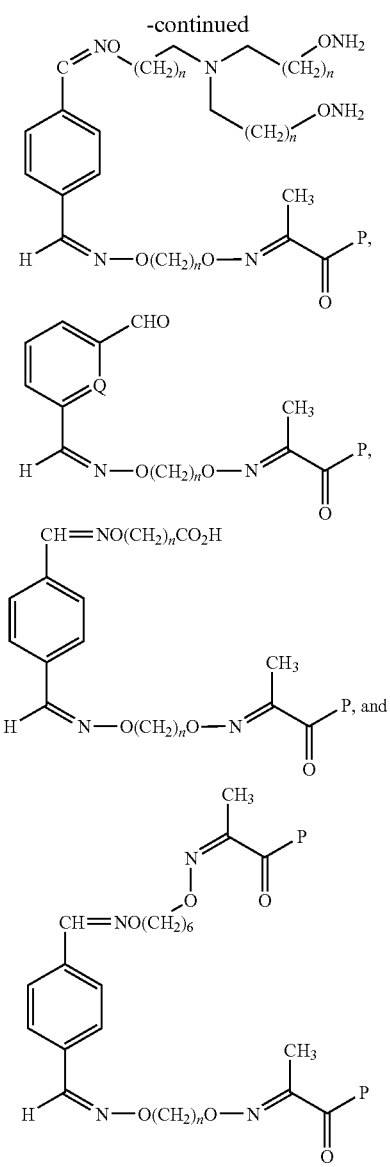

In some embodiments, P is selected from the group consisting of granulocyte macrophage colony-stimulating factor, human superoxide dismutase, annexin proteins, leptin proteins, myoglobin, albumin, avidin, and an enzyme or a receptor.

In another aspect, the invention provides a compound of the formula:

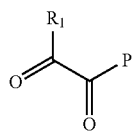

wherein,

P is selected from the group consisting of granulocyte macrophage colony-stimulating factor, human superoxide dismutase, annexin, leptin, myoglobin, albumin, avidin, and an enzyme or antibody, and $R_1$ is selected from the group consisting of hydrogen, methyl or amino acid side chain.

In various embodiments, the invention includes compounds where P is an annexin protein. In some embodiments, P is an annexin V protein.

The compounds can be further substituted with a therapeutic agent, a diagnostic agent, a solid support, or any combination thereof. The therapeutic agent or diagnostic agent can be a radionucleotide, small molecule therapeutic agent, antibody, optical label, fluorescent label, biosynthetic label, or oligonucleotide. The diagnostic agent can be a NOTA or DOTA chelate of gallium or technetium, Cu-64, Ga-67, Ga-68, Zr-89, Ru-97, Tc-99m, Rh-105, Pd-109, In-111, I-123, I-125, I-131, Re-186, Re-188, Au-198, Au-199, Pb-203, At-211, Pb-212, Bi-212, fluorochrome, fluorescein, rhodamine, Texas Red®, phycobiliproteins, [$^{18}$F] benzaldehyde, [$^{18}$F] labeled fluoro-2-deoxyglucose (FDG), tetraacetyl fluoroglucose (TAFg), or a fluorescent resonance energy transfer (FRET) donor or acceptor. The solid support can comprise agarose, styrene or Tentagel.

In some embodiments, the therapeutic or diagnostic agent is selected from the group consisting of:

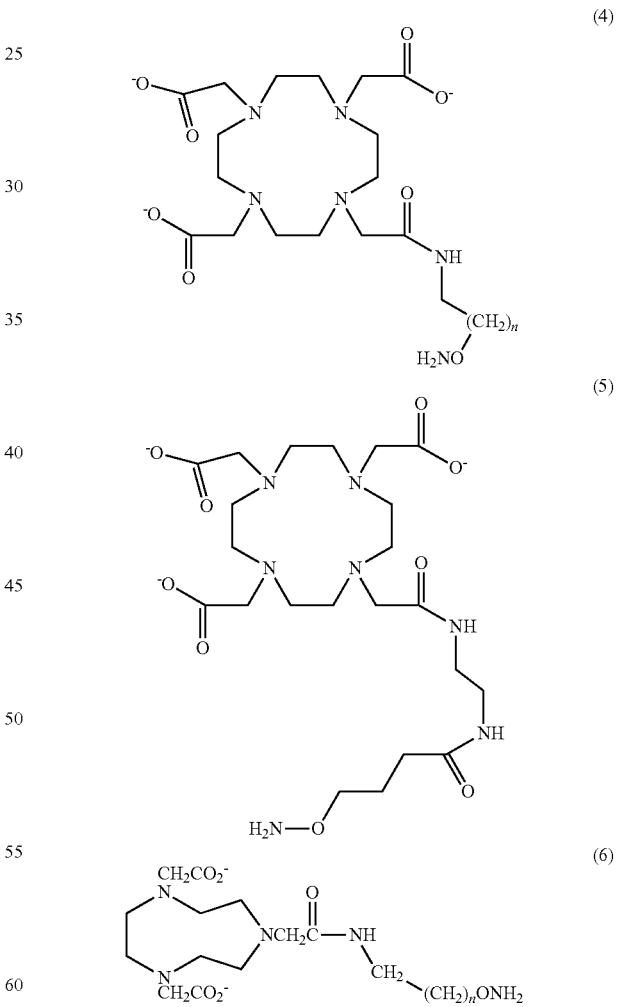

In another aspect, the invention provides a method of therapy or medical diagnostics comprising administering to a subject in need thereof a compound as described above. In yet another aspect, the invention provides a pharmaceutical composition comprising a compound as described above, and a pharmaceutically acceptable carrier or diluent. In another aspect, the invention provides a method for noninvasive measurement of apoptosis, the method comprising the steps of: administering the compound as described above to a patient containing a target cell group; obtaining an image of the target cell group; and evaluating the image to determine an amount of cell death within the target cell group.

In another aspect, the invention provides a method of prediction of cell death, the method comprising the steps of: administering a compound as described above to a patient containing the target cell group; obtaining an image of the target cell group; and evaluating the image to determine an amount of cell death within the target cell group. In yet another aspect, the invention provides a method of treating a subject suffering from or at risk of atherothrombosis, plaque rupture, arthritis, Crohn's disease or cancer, comprising administering to said subject a pharmaceutical composition comprising an effective amount of a compound as described above.

In another aspect, the invention provides a method of forming a compound of any one of the preceding claims comprising, reacting a peptide, polypeptide, or protein with a compound comprising a carbonyl group capable of transamination, such that the corresponding N-terminal α-carbonyl amide derivative is obtained. The method as described above further can include, reacting the N-terminal α-carbonyl amide derivative with an alkoxy amine, a hydrazine or a semicarbazide group, such that the corresponding oxime, hydrazone or semicarbazone is obtained.

In some embodiments of the method, the annexin protein is an annexin V protein. In some embodiments of the method, the compound comprising a carbonyl group capable of transamination is pyridoxal phosphate.

In another aspect, the invention provides a modified annexin protein comprising an annexin protein terminating with an α-ketoamide or α-aldoamide. In another aspect, the invention provides a modified annexin protein comprising an annexin protein terminating with an oxime, hydrazone or semicarbazone.

In some embodiments of the method, the modification occurs at the N-terminus. In some embodiments of the method, the N-terminus comprises alanine, glycine, or formylglycine. The modified annexin protein as described above, can be multiply-substituted with a plurality of aminoxy, carbonyl, hydrazine or semicarbazide groups, or any combination thereof. The modified annexin protein as described above, can be substituted with at least one dendrimer consisting of an aminoxy group.

In another aspect, the invention provides a modified protein comprising a moiety of formula III at the N-terminus:

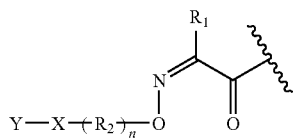

III wherein, $R_1$ is selected from the group consisting of hydrogen, methyl, and amino acid side chain, $R_2$ is independently selected from the group consisting of optionally substituted $C_1$-$C_{20}$ alkyl, $C_2$-$C_{20}$ alkenyl, and $C_2$-$C_{20}$ alkynyl, X is selected from the group consisting of a covalent bond, O, NR, CO, and NRCO, Y is selected from the group consisting of $OR_3$, $NR_3R_3$, $N(R_3)NR_3R_3$, and $N=CR_3Z$, R is selected from the group consisting of hydrogen, $C_1$-$C_{20}$ alkyl, $C_2$-$C_{20}$ alkenyl, $C_2$-$C_{20}$ alkynyl, aryl, cycloalkyl, and heterocycloalkyl, Z is selected from the group consisting of $R_5$—$R_4$—$R_3$, and optionally substituted aryl, $R_3$ is selected from the group consisting of hydrogen, $C_1$-$C_{20}$ alkyl, $C_2$-$C_{20}$ alkenyl, and $C_2$-$C_{20}$ alkynyl, $R_4$ is selected from the group consisting of a covalent bond, O, NR, CO, and NRCO, $R_5$ is selected from the group consisting of $OR_6$, $NR_6R_6$, $N(R_6)NR_6R_6$, and $N=CR_6R_6$, $R_6$ is independently selected from the group consisting of hydrogen, $C_1$-$C_{20}$ alkyl, $C_2$-$C_{20}$ alkenyl, and $C_2$-$C_{20}$ alkynyl, n is 1-21, ⁓ identifies the remainder of the substituted protein structure, and each optional substitution is selected from the group consisting of optionally radioactive F, Cl, Br, I, OR, SR, COR, NRR, OAr, and NHAr.

In another aspect, the invention provides a method of making fusion proteins comprising, reacting a first peptide containing an aminoxy, a hydrazine or a semicarbazide group with a first aldehyde group of a compound containing at least two aldehyde groups. The method can include, reacting a second peptide containing an aminoxy, a hydrazine or a semicarbazide group with a second aldehyde group of the compound containing at least two aldehyde groups. In some embodiments of the method, the first peptide is annexin V. In some embodiments of the method, the aminoxy, hydrazine or semicarbazide group is at the N-terminus of annexin V.

In another aspect, the invention provides a modified protein comprising a moiety of formula IV at the N-terminus:

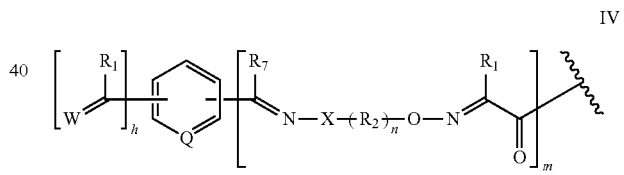

IV wherein, $R_1$ is independently selected from the group consisting of hydrogen, methyl and α-amino acid side chain, $R_2$ is independently selected from the group consisting of optionally substituted $C_1$-$C_{20}$ alkyl, $C_2$-$C_{20}$ alkenyl, and $C_2$-$C_{20}$ alkynyl, X is selected from the group consisting of a covalent bond, O, NR, CO, and NRCO, W is selected from the group consisting of $OR_3$, $NR_3R_3$, $NOR_3$, $NOR_3N(R_3ONR_3)_2$ and $N=CR_3Z$, Q is CH or N, R is selected from the group consisting of hydrogen, $C_1$-$C_{20}$ alkyl, $C_2$-$C_{20}$ alkenyl, $C_2$-$C_{20}$ alkynyl, aryl, cycloalkyl, and heterocycloalkyl, Z is selected from the group consisting of $R_5$—$R_4$—$R_3$, and optionally substituted aryl, $R_3$ is selected from the group consisting of hydrogen, $C_1$-$C_{20}$ alkyl, $C_2$-$C_{20}$ alkenyl, and $C_2$-$C_{20}$ alkynyl, $R_4$ is selected from the group consisting of a covalent bond, O, NR, CO, and NRCO, $R_5$ is selected from the group consisting of $OR_6$, $NR_6R_6$, $N(R_6)NR_6R_6$, and $N=CR_6R_6$, $R_6$ is independently selected from the group consisting of hydrogen, $C_1$-$C_{20}$ alkyl, $C_2$-$C_{20}$ alkenyl, and $C_2$-$C_{20}$ alkynyl, $R_7$ is hydrogen or methyl, n is 1-21, m is 0-3, h is 0-3 provided that at least one m or at least one h is 1, 〜 identifies the remainder of the substituted protein structure, and each optional substitution is selected from the group consisting of optionally radioactive F, Cl, Br, I, OR, COR, NRR, OAr, and NHAr.

In another aspect, the invention provides a method of making fusion proteins comprising, reacting a protein terminating with an α-ketoamide or α-aldoamide with a mono-oxime conjugate containing an aminoxy terminal side chain. In certain embodiments a free carbonyl has been introduced chemospecifically into the first protein which reacts with a second protein containing an α-nucleophile. In some embodiments, the fusion protein can be homodimeric. In certain embodiments, the fusion protein can be heterodimeric. In various embodiments, the fusion protein is formed with retention of biological activity.

In another aspect, the invention provides a modified protein comprising a compound of formula V:

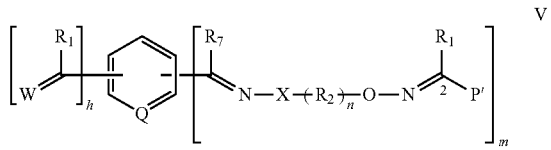

and any isomers thereof, wherein, $R_1$ is independently selected from the group consisting of hydrogen, alkyl and α-amino acid side chain, P' is a protein optionally modified to contain a carbonyl group at carbon 2, $R_2$ is independently selected from the group consisting of optionally substituted $C_1$-$C_{20}$ alkyl, $C_2$-$C_{20}$ alkenyl, and $C_2$-$C_{20}$ alkynyl, X is selected from the group consisting of a covalent bond, O, NR, CO, and NRCO, W is selected from the group consisting of O, $NOR_3$, $NOR_3N(R_3ONR_3)_2$ and $N=CR_3Z$, Q is CH or N, R is selected from the group consisting of hydrogen, $C_1$-$C_{20}$ alkyl, $C_2$-$C_{20}$ alkenyl, $C_2$-$C_{20}$ alkynyl, aryl, cycloalkyl, and heterocycloalkyl, Z is selected from the group consisting of $R_5$—$R_4$—$R_3$, and optionally substituted aryl, $R_3$ is selected from the group consisting of hydrogen, $C_1$-$C_{20}$ alkyl, $C_2$-$C_{20}$ alkenyl, and $C_2$-$C_{20}$ alkynyl, $R_4$ is selected from the group consisting of a covalent bond, O, NR, CO, and NRCO, $R_5$ is selected from the group consisting of $OR_6$, $NR_6R_6$, $N(R_6)NR_6R_6$, and $N=CR_6R_6$, $R_6$ is independently selected from the group consisting of hydrogen, $C_1$-$C_{20}$ alkyl, $C_2$-$C_{20}$ alkenyl, and $C_2$-$C_{20}$ alkynyl, $R_7$ is hydrogen or methyl, n is 1-21, m is 0-3, h is 0-3 provided that at least one m or at least one h is 1, and each optional substitution is selected from the group consisting of optionally radioactive F, Cl, Br, I, OR, NRR, COR, OAr, and NHAr.

In certain embodiments, P' represents a protein that has been or that can be modified to contain

such that it can be reacted to form a compound of formula V.

In another aspect, the invention provides a kit comprising a pharmaceutical composition as described above; and, instructions for using the pharmaceutical composition for treating atherothrombosis, plaque rupture, arthritis, Crohn's disease or cancer.

In one aspect the present invention describes the site-specific chemical modification of annexin proteins at their N-termini with high conversion. In some embodiments, the present invention describes the formation of homogeneous adducts. The present invention can be applied to proteins such as annexins with natural amino acid sequences containing alanine at the N-terminal (e.g., annexins I, III, IV, V, VI and VIII). The present invention can also be applied to mutant annexins with formylglycine, glycine or alanine N-terminal amino acids.

Thus, in various embodiments, one or more effectors, such as a diagnostic agent, a therapeutic agent, a chemotherapeutic agent, a radioisotope, an imaging agent, an anti-angiogenic agent, a cytokine, a chemokine, a growth factor, a drug, a prodrug, an enzyme, a binding molecule, a ligand for a cell surface receptor, a chelator, an immunomodulator, an oligonucleotide, an interference RNA, an aptamer, a hormone, a photodetectable label, a dye, a peptide, a toxin, a contrast agent, a paramagnetic label, an ultrasound label, a pro-apoptotic agent, a liposome, a nanoparticle or a combination thereof, may be attached to an N-terminally modified protein as described herein.

The foregoing brief summary broadly describes the features and technical advantages of certain embodiments of the present invention. Further technical advantages will be described in the detailed description of the invention that follows. Novel features that are believed to be characteristic of the invention will be better understood from the detailed description of the invention when considered in connection with any accompanying figures and examples. However, the figures and examples provided herein are intended to help illustrate the invention or assist with developing an understanding of the invention, and are not intended to be definitions of the invention's scope.

DETAILED DESCRIPTION OF THE INVENTION

Figure 1:
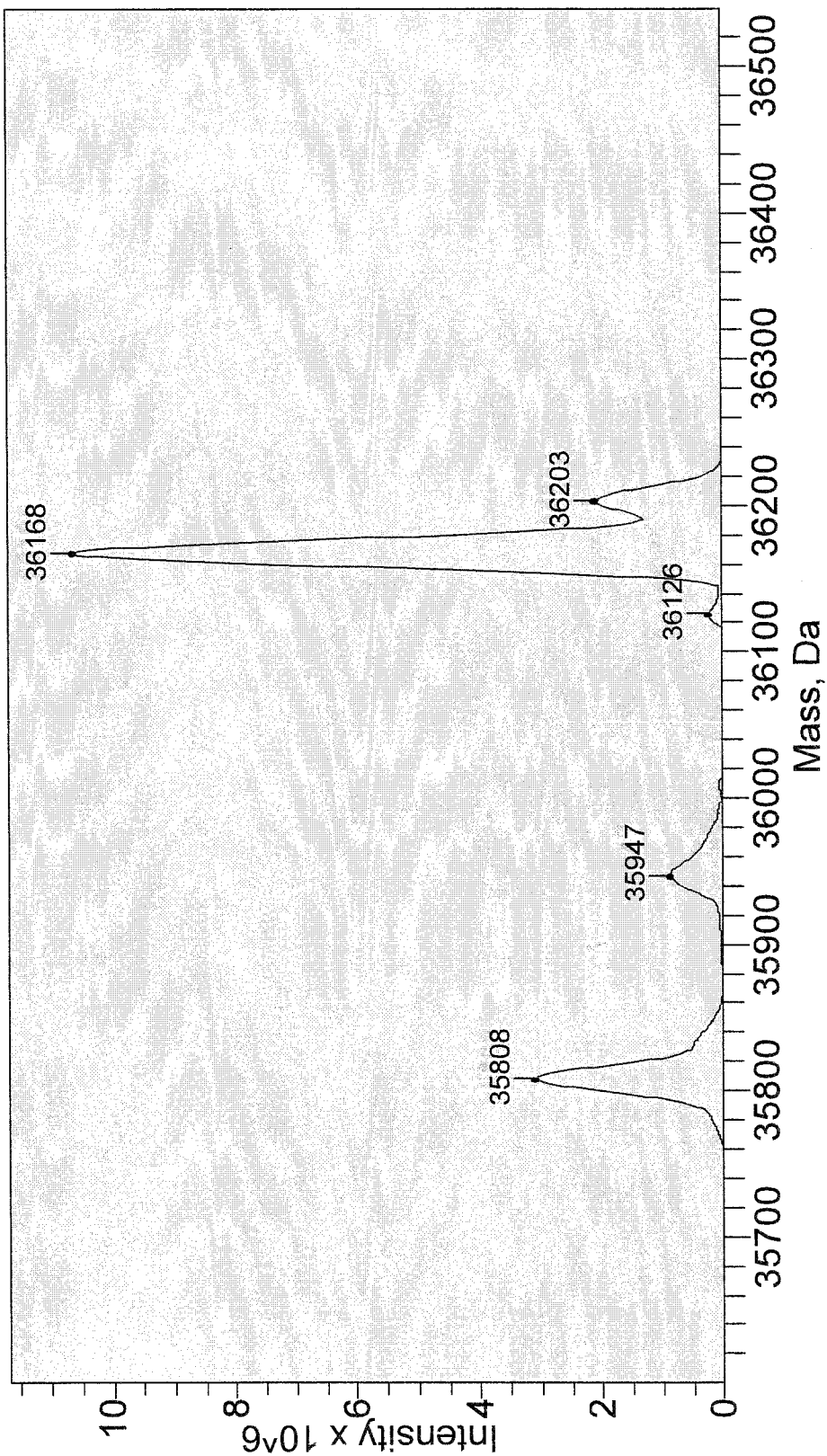
FIGS. 1, 2 and 3 show mass spectral images depicting the modified proteins described herein.

The term "treat," "treated," "treating" or "treatment" includes the reduction, diminishment or alleviation of at least one symptom associated or caused by the state, disorder or disease being treated. In certain embodiments, the treatment comprises the induction of a disorder, followed by the activation of the compound of the invention, which would in turn diminish or alleviate at least one symptom associated or caused by the disorder being treated. For example, treatment can be diminishment of one or several symptoms of a disorder or complete eradication of a disorder.

The term "subject" is intended to include organisms, e.g., prokaryotes and eukaryotes, which are capable of suffering from or afflicted with a disease, disorder or condition. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancer, arthritis, atherothrombosis, plaque rupture, or Crohn's disease. In another embodiment, the subject is a cell.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Furthermore, the expression "$C_x$-$C_y$-alkyl", wherein x is 1-5 and y is 2-20 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl.

The term "alkenyl," alone or in combination refers to a straight-chain, cyclic or branched hydrocarbon residue comprising at least one olefinic bond and the indicated number of carbon atoms. Preferred alkenyl groups have up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl, isobutenyl, 1-cyclohexenyl, 1-cyclopentenyl.

The term "alkynyl" includes unsaturated aliphatic groups analogous in length to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

The term "aryl," generally represented as "Ar," includes aromatic monocyclic or multicyclic e.g., tricyclic, bicyclic, hydrocarbon ring systems consisting only of hydrogen and carbon and containing from six to nineteen carbon atoms, or six to ten carbon atoms, where the ring systems can be partially saturated. Aryl groups include, but are not limited to, groups such as phenyl, tolyl, xylyl, anthryl, naphthyl and phenanthryl. Aryl groups can also be fused or bridged with alicyclic or heterocyclic rings which are not aromatic so as to form a polycycle (e.g., tetralin). In certain embodiments, the aryl group can be directly attached to an oxygen atom "OAr" so as to form an aryloxy group. For example a phenoxyl group where a phenyl ring is attached to an oxygen atom.

The terms alkoxylamine and aminoxy group are used interchangeably herein and generally describe a species containing the moiety, $CH_2ONH_2$ The term α-carbonyl amide is meant to describe an α-ketoamide or an α-aldoamide The term "peptide" includes chains of amino acids linked by peptide bonds. The term "peptide" can also refer to a "protein" or "polypeptide" (e.g., annexin proteins, granulocyte macrophage colony-stimulating factor, human superoxide dismutase, leptin, myoglobin, albumin, avidin, and an enzyme), which are compounds made of amino acids arranged in a linear chain and folded into a globular form.

A variety of polypeptides or proteins may be used within the scope of the methods and compositions provided herein. In certain embodiments, the proteins may comprise antibodies or fragments of antibodies containing an antigen-binding site. As used herein, a protein, polypeptide or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide" and "peptide" are used interchangeably herein. Accordingly, the term "protein or peptide" encompasses amino acid sequences comprising at least one of the common amino acids found in naturally occurring proteins, or at least one modified or unusual amino acid.

The term "α-amino acid side chain" includes the naturally occurring α-amino acids with side chains, such as for example, an alanine residue that includes a methyl group as a side chain. The side chain can also be any side chain of an unnatural amino acid. A variety of unnatural amino acids containing side chains are known to one of skill in the art. A skilled artisan appreciates various other α-amino acid side chains.

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The protein, polypeptide and peptide sequences can be found at computerized databases known to those of ordinary skill in the art. One such database is the National Center for Biotechnology Information's Genbank and GenPept databases (www.ncbi.nlm.nih.gov/). Alternatively, various commercial preparations of proteins, polypeptides, and peptides are known to those of skill in the art.

The term "fusion protein" includes a single molecular entity having at least two polypeptide domains that are not normally present in a single, natural polypeptide. Thus, naturally occurring proteins are not "fusion proteins", as used herein.

The term "alpha nucleophile" includes a nucleophile bearing an unshared pair of electrons on an atom adjacent to the nucleophilic site.

The term "carrier" includes natural or synthetic molecules or aggregates thereof which can be associated covalently or non-covalently with therapeutic, diagnostic, or research compounds. Carriers also include, but are not limited to chelators, natural or synthetic polymers including dendrimers, co-polymers, derivatized polymers, liposomes, various viral and bacteriophage particles, various natural and manufactured nano- and microparticles, and beads.

The present invention includes all isomeric (e.g., enantiomeric, diastereomeric, and geometric (or conformational)) forms of the compounds; for example, syn and anti isomers, the R and S configurations for each asymmetric center, Z and E double bond isomers, and Z and E conformational isomers. Therefore, single stereochemical isomers as well as enantiomeric, diastereomeric, and geometric (or conformational)

mixtures of the present compounds are within the scope of the invention. Unless otherwise stated, all tautomeric forms of the compounds of the invention are within the scope of the invention.

The present invention includes all pharmaceutically acceptable isotopically-labeled compounds of the invention, wherein one or more atoms are replaced by atoms having the same atomic number, but an atomic mass or mass number different from the atomic mass or mass number usually found in nature.

Examples of isotopes suitable for inclusion in the compounds of the invention comprises isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

The compositions provided herein also include pharmaceutically acceptable salts of those compositions. Salts derived from appropriate bases include alkali metal, alkaline earth metal, and ammonium salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Methods of Preparation
Chemical Modification of Proteins

The present invention provides site-specific modifications of proteins. In particular, the N-termini of proteins can be modified. In some preferred embodiments, the N-termini of the protein can include a glycine or alanine side chain.

In various embodiments, the amino group at the N-termini of proteins can undergo a transamination reaction to form the corresponding α-carbonyl amide. In certain preferred embodiments, the α-carbonyl amide can be an α-ketoamide or an α-aldo amide.

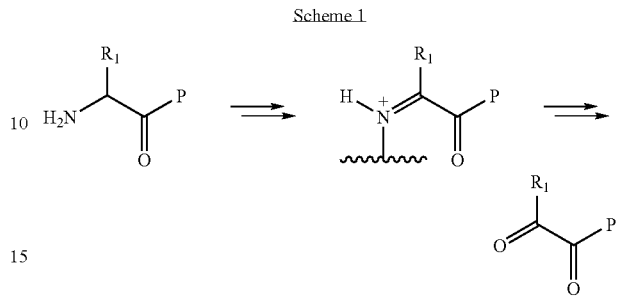

Scheme 1

As shown in scheme 1, the N-terminal amino group of a protein can be converted to the corresponding carbonyl group via an activation step. For scheme 1 and all schemes listed below, P can be a protein or part of a protein such as granulocyte macrophage colony-stimulating factor, human superoxide dismutase, an annexin protein or leptin. $R_1$ is selected from the group consisting of hydrogen, methyl, or natural α-amino acid side chains.

The transamination reaction can be carried out in a stepwise manner via the formation of the corresponding iminium ion followed by hydrolysis and/or oxidation. In various embodiments, the transamination reaction can be performed enzymatically or by chemical agents. In certain embodiments, the transamination reaction is performed using pyridoxal phosphate (PLP).

In a general method, the protein is dissolved in a suitable solvent or buffer. For example, for the transamination reaction, a desired amount of the protein solution is incubated with PLP for about 1-20 hours at a pH of about 3-11 and at a temperature of about 10-60° C. After the incubation is complete, the solution can be subjected to centrifuge filtration. Removal of the excess reagents followed by optional purification provides the corresponding α-carbonyl amide.

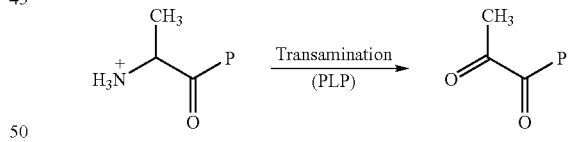

Scheme 2

Scheme 2 provides a specific example of a site specific N-terminal transamination and oxidation of granulocyte macrophage colony-stimulating factor, human superoxide dismutase, an annexin protein or leptin proteins containing an N-terminal alanine side chain, leading to a pyruvyl protein. Transamination of proteins such as granulocyte macrophage colony-stimulating factor, human superoxide dismutase, an annexin protein or leptin affords several additional possibilities for functionalizing the carbonyl group obtained at the N-terminus. In certain embodiments, the chemo selective conversion of the α-ketoamide to oximes using aminooxy substrates can be carried out. For example, as shown in scheme 3, condensation of the α-ketoamide with am-bis-aminoxy substrates results in the corresponding mono oxime conjugate containing an aminoxy terminal side chain. The latter aminoxy group allows for further modifications of the conjugated protein. In some embodiments, dimers can be prepared between a transaminated protein and the aminoxy containing conjugates of Scheme 3 when proteins have a tendency to dimerize. For example, dimers of leptin proteins can be prepared. In some embodiments, a hydrazine or semicarbazide can be used to form conjugates other than an oxime, since reaction of a hydrazine or semicarbazide with the α-carbonyl group at the protein N-terminus can provide the corresponding hydrazone or semicarbazone respectively.

In various embodiments, homodimeric or heterodimeric fusion proteins can be formed site-specifically through the agency of a mono-oxime conjugate containing an aminoxy terminal side chain as shown in scheme 3. For example, the tethered alkoxylamine in a first molecule of (9) can be combined with a di-carboxaldehyde like terephthaldehyde to give the tethered aldehyde (15) which, in turn, can be combined with a second molecule of (9) to give the fusion protein.

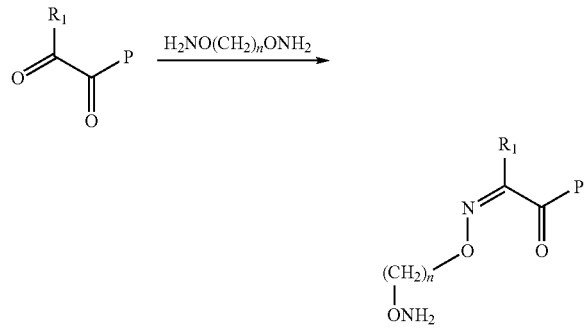

In certain embodiments, the additional group for further modification can be a hydrazine or a semicarbazide, instead of an alkoxylamine. Further modification of the product can include reacting the additional group with (i) another protein containing an α-carbonyl group, or (ii) with another protein or small molecule compound containing a carbonyl group. The resulting product can contain an additional hydrazone, or semicarbazone.

In certain embodiments, instead of using a bis-aminoxy compound, the α-ketoamide can be treated with a compound containing at least two moieties selected from the group consisting of aminoxy, hydrazine and semicarbazide. The resulting oxime, hydrazone or semicarbazone can contain an additional aminoxy, hydrazine or semicarbazide that can be further reacted with (i) another protein containing an α-carbonyl group, or (ii) with another compound such as, for example, protein or small molecule containing a carbonyl group.

In a general method, the α-carbonyl amide is dissolved in a suitable solvent or buffer. A desired amount of the α-carbonyl amide solution is incubated with a solution containing the bis-aminoxy compound for about 1-24 hours at a pH of about 3-11 and at a temperature of about 10-60° C. After the incubation is complete, the solution is subjected to centrifuge filtration. Removal of the excess reagents followed by optional purification provides the corresponding aminoxy-oxime product.

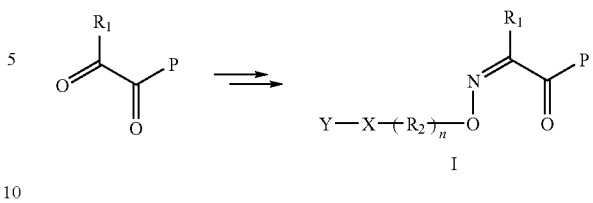

As shown in scheme 4, the α-carbonyl group at the N-terminal can be converted to the corresponding oxime derivative of formula I where P is selected from the group consisting of granulocyte macrophage colony-stimulating factor, human superoxide dismutase, annexin and leptin, $R_1$ is selected from the group consisting of hydrogen, methyl and α-amino acid side chain, $R_2$ is independently selected from the group consisting of optionally substituted $C_1$-$C_{10}$ alkyl, alkenyl, and alkynyl, X is selected from the group consisting of a covalent bond, O, NR, CO, and NRCO, Y is selected from the group consisting of $OR_3$, $NR_3R_3$, $N(R_3)NR_3R_3$, and $N=CR_3Z$, R is selected from the group consisting of hydrogen, $C_1$-$C_{10}$ alkyl, alkenyl, alkynyl, aryl, cycloalkyl, and heterocycloalkyl, Z is selected from the group consisting of $R_5$—$R_4$—$R_3$, and optionally substituted aryl, $R_3$ is selected from the group consisting of hydrogen, $C_1$-$C_{20}$ alkyl, alkenyl, and alkynyl, $R_4$ is selected from the group consisting of a covalent bond, O, NR, CO, and NRCO, $R_5$ is selected from the group consisting of $OR_3$, $NR_3R_3$, $N(R_3)NR_3R_3$, and $N=CR_3R_3$, n is 1-21, and each optional substitution is selected from the group consisting of optionally radioactive F, Cl, Br, I, OR, SR, NRR, OAr, and NHAr.

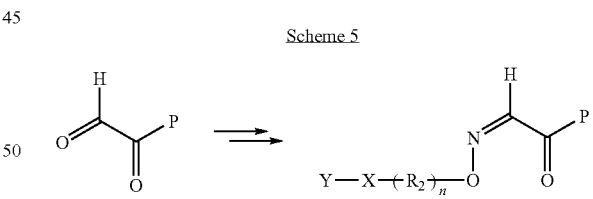

In some embodiments, the corresponding aldoximes can be formed from glycine N-terminals (i.e., $R_1$ is hydrogen) and alkoxylamines as shown in scheme 5. The use of β-mercaptoethanol and dithiothreitol can sometimes reverse the formation of the aldoximes. An adduct corresponding to a 1:1 complex between the carbonyl amide and the thiol reagent can be formed. An advantage of such a method is that it provides a means of detaching proteins, in aldoxime linkage, from solid surfaces so that they can be evaluated analytically after chemical modification and/or other treatments.

The formation of α-aldo- or α-keto-amides can allow for irreversible, specific attachment of certain aminoxy-substrates to the α-carbonyl of the transaminated protein. Most notably a variant can be made as shown in scheme 6 of a synthetic precursor to the imaging agent NOTA by linking a chain to one of the ring carboxyls in (1), or off one of the α-carbons (linkage not shown). The ultimate conjugate with a protein, for example, the preparation of the corresponding NOTA adduct of annexin V, can be formed with (3).

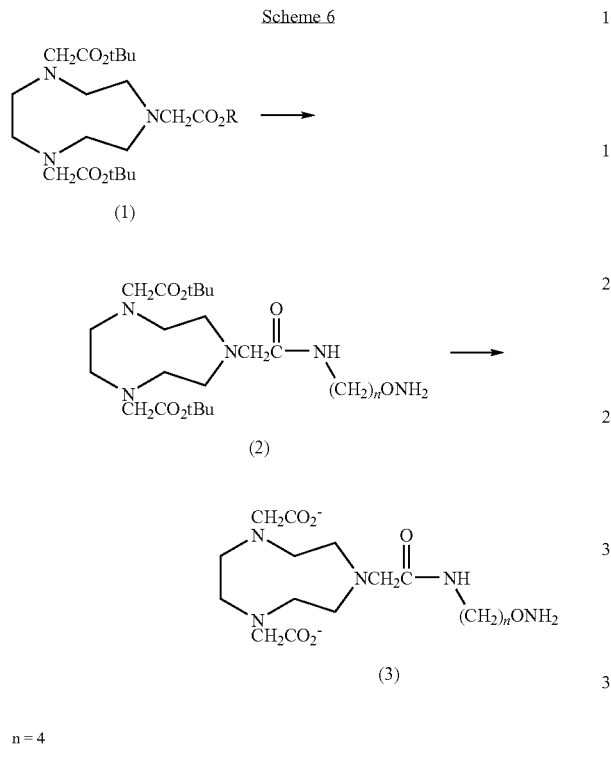

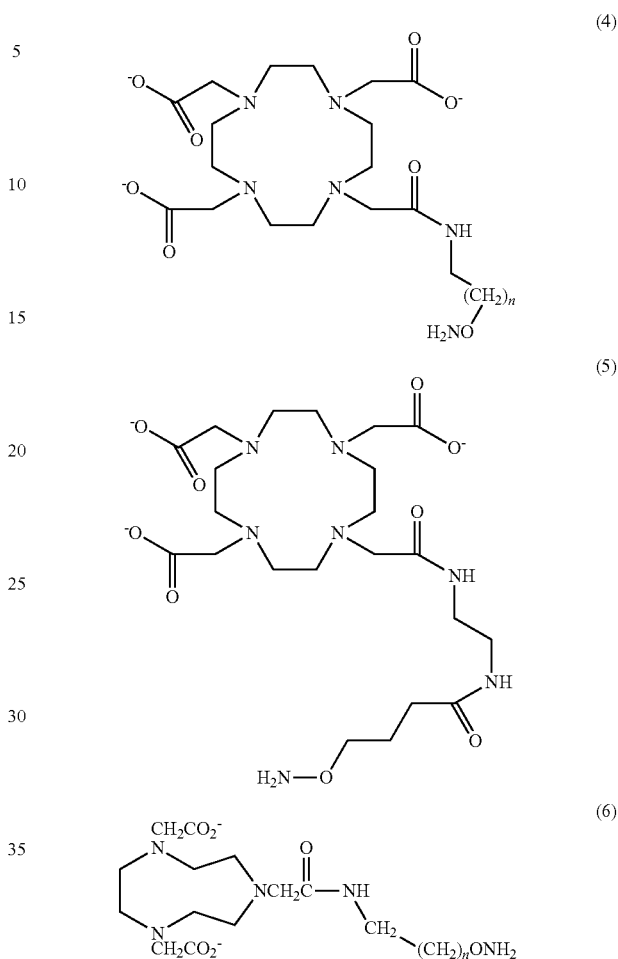

In certain embodiments, the reactions with aminoxy substrates are conducted under a variety of conditions, using for example, PLP and other imine forming agents. In some embodiments, the reaction can be conducted at temperatures from 25-50 degrees Celsius, at a pH range from 6-8. The reaction can display conversions from 60-80%. For example, the reaction with PLP to give a ketoamide can be accomplished with 60% conversion within 4 hours. The ketoamide can then be converted overnight to the target oxime with a variety of O-substituted hydroxylamines. The heterocycle (1), with one free carboxyl (R=H), can be synthesized as described in "A General Synthesis of Mono- and Disubstituted 1,4,7-Triazacyclononanes" Tetrahedron Letters 36, 9269-9272 (1995) by Z. Kovacs and D. Sherry. Condensation of appropriately activated forms of (1) using carbodiimide reagents with bifunctional α,ω-amino-alkoxylamines (in which the aminoxy function has been selectively protected), followed by deprotection, gives (3). Some specific target molecules (n=3-8) that can be extended by functionalized carboxyl side chains, and form oxime adducts that represent potential imaging agents or therapeutics, are shown in scheme 7. Analogous molecules with side chains appended to α-CH of an intact acetate moiety can be envisaged and prepared by chemists of ordinary skills, trained in the art.

As indicated above for NOTA and DOTA entities (4)-(6), the nucleophilic aminoxy group is a preferred choice for incorporation of the substrate containing the chelating moiety to the transaminated protein containing the activated carbonyl. However, electrophilic entities can also be used as substrate to conjugate to the protein framework because of their commercial availability or synthetic utility. For example, strategies that utilize radioactive [$^{18}$F]-labeled aldehyde substrates can be linked through their carbonyl functions to a—protein target incorporating an aminoxy function.

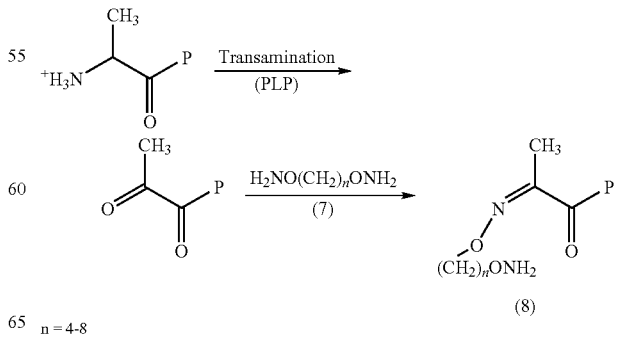

where P is e.g., characteristic of granulocyte macrophage colony-stimulating factor, human superoxide dismutase, an annexin protein or leptin.

In certain embodiments, oximes of the pyruvyl proteins such as (8) in Scheme 8 can be formed using α,ω-bis-aminoxysubstrates (7, n=4-8). In some preferred embodiments, n is 5-7. In various preferred embodiments, n is 6. The advantage of this method is that oxime formation occurs smoothly and is site-specific and virtually quantitative. In certain embodiments, aniline or ethylene diamine can act as a catalyst to accelerate conjugate formation. The conjugates (8) can provide a practical basis for rapidly and site-specifically condensing numerous aldehydes exemplified by (10) onto the extended protein framework to give homogeneous adducts. It will be appreciated that that claims embodied by conjugation of aldehydes to modified proteins apply as well to analogous methylketones. Either carbonyl moiety, once installed is capable of undergoing adduct formation as described herein, at many other sites along the protein surface

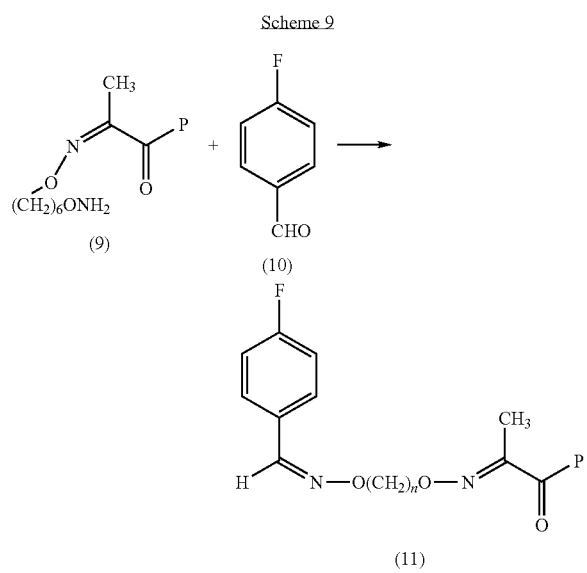

As shown in scheme 9, 4-fluoro-benzaldehyde (10) reacts completely with (9, (8, n=6)). Indeed, with annexin V the reaction of (9, (8, n=6)) with aldehyde (10) to form the corresponding aryl aldoxime product (11) occurs specifically and quantitatively with the aminoxy function, within minutes. Such rapid rates make it feasible for attaching [$^{18}$F]-4-fluorobenzaldehyde to a transaminated protein such as annexin V through the agency of (9) by the sequence in scheme 8, allowing for the formation of potential imaging agents. In one embodiment, the reaction of (10) has utility with respect to the radionuclide to produce diagnostic imaging agents with annexin V for Positron Emission Tomography (PET) as well as in the manufacture of kits. In some embodiments, $^{18}$F-labeled fluorodeoxyglucose can be used analogously in the formation of potential imaging agents. See "Review of $^{18}$F-FDG synthesis and quality control," by S. Yu, Biomedical Imaging and Intervention Journal, 2006; 2(4): e57. In a general sense, this sequence featuring condensation of a bis-nucleophile with an α-carbonyl, constitutes a method of reversing the polarity of the transaminated protein: it introduces a highly nucleophilic entity such as aminoxy, to allow the attachment of electrophiles.

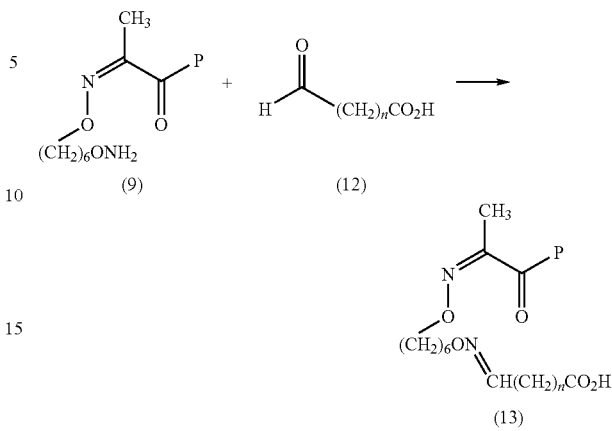

Scheme 10 shows another embodiment where the aminoxy group of (9) forms an oxime with an aldehyde group. The reaction of the ω-aldoalkanoic acid can also proceed in like manner to (10). This process is useful, for example, because it provides a basis for depositing proteins on human serum albumin to increase their duration of action. The carboxylic group at either terminal end of the fatty acid chain in (13) (shown only for the distal end) can be targeted for human serum albumin binding sites to increase the duration of action in vivo of a biologically active protein P. (Dennis M S, Zhang M, Meng Y G, Kadkhodayan M, Kirchhofer D, Combs D, Damico L A. Albumin binding as a general strategy for improving the pharmacokinetics of proteins. J Biol. Chem. 2002 277(38):35035-43.).

The rapid rates of reaction of proteins containing aminoxy nucleophiles with aldehydes can also be exploited with aryl poly-aldehydes and can afford a convenient method for introducing aldehyde functions onto the extended protein framework. For example, as shown in Scheme 11, terephthaldehyde (14), isophthaldehyde (16), 2,6-diformylpyridine (17), and 1,3,5-triformylbenzene (18) can be linked to proteins, e.g., annexin V (9) to form conjugates (15) and (19)-(21), respectively, in excellent yields without significant competition from secondary reactions that consume the remaining aldehyde functions.

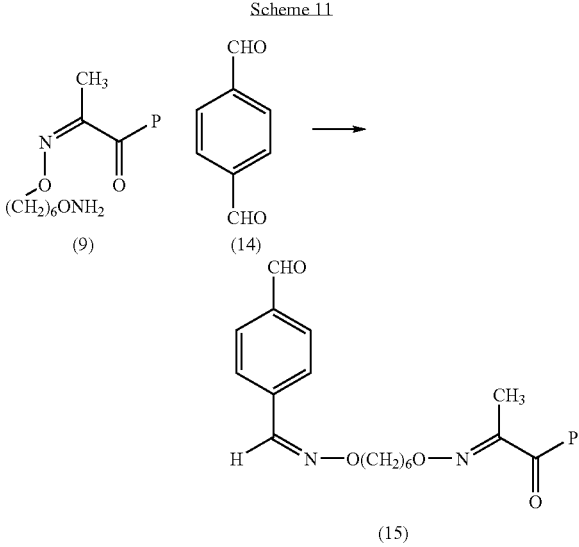

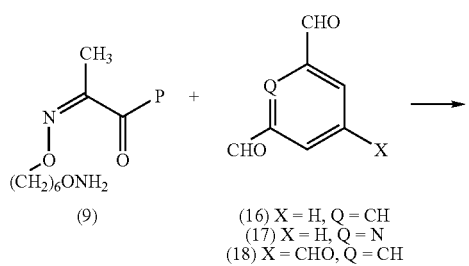

(9)

(16) X = H, Q = CH
(17) X = H, Q = N
(18) X = CHO, Q = CH

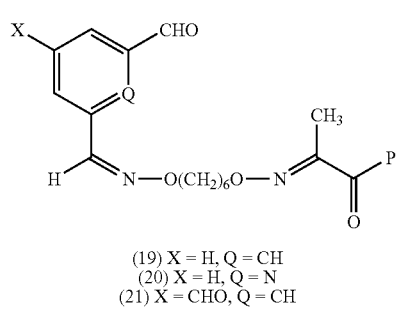

(19) X = H, Q = CH
(20) X = H, Q = N
(21) X = CHO, Q = CH

The methodology involving aryl polyaldehydes constitutes a method of reversing the polarity of the dominant nucleophilic reactivity of the protein to useful and apparently stable electrophilic (aldehydic) functionality.

The potential utility of this methodology can more generally be appreciated by reference to Scheme 12 in which the functionalized protein (P-A) is elaborated in successive cycles to a protein with a multifunctional side-chain containing additional A and/or B components. (A cycle is defined herein to mean a round of aldehyde coupling to the protein followed by aminoxy coupling to the aldehyde components of the protein, or vice versa.)

As shown in Scheme 12 using 1,3,5-triformylbenzene as the polyaldehyde substrate, a single cycle from P-A to P-A-B(A)(A) doubles the number of free aminoxy groups. As well, P-A-B with two free formyl groups is elaborated to P-A-B-(A-B)(A-B) containing four free formyl groups. Scheme 13 demonstrates the quadrupling of the components A and B through a single cycle. Because of the facility with which condensations between aminoxy and aldehyde groups occur, this method can afford the opportunity of introducing multiple equivalents of drugs, imaging agents and the like directly onto the protein framework, e.g., 4-fluorobenzaldeyde with aminoxyproteins, or (3, n=4) with aldehydic proteins, or -via derivatized forms of aminoxy or aldehyde substrates A and B, respectively, onto a carrier protein or polypeptide.

Scheme 12

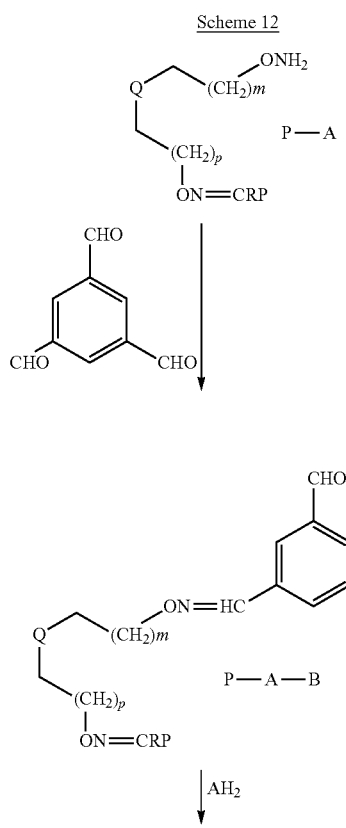

-continued
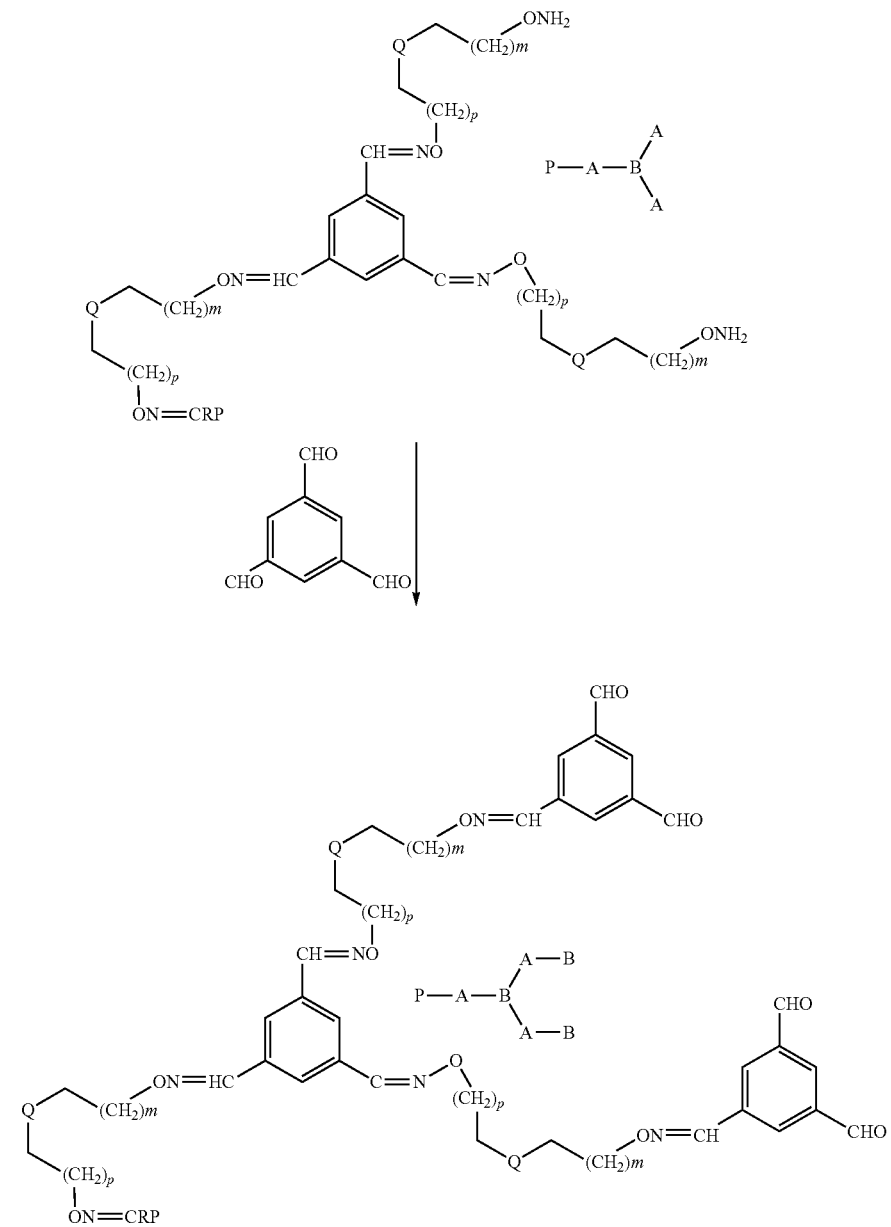
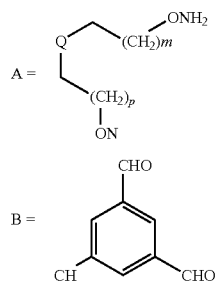
Q = N, alkyl

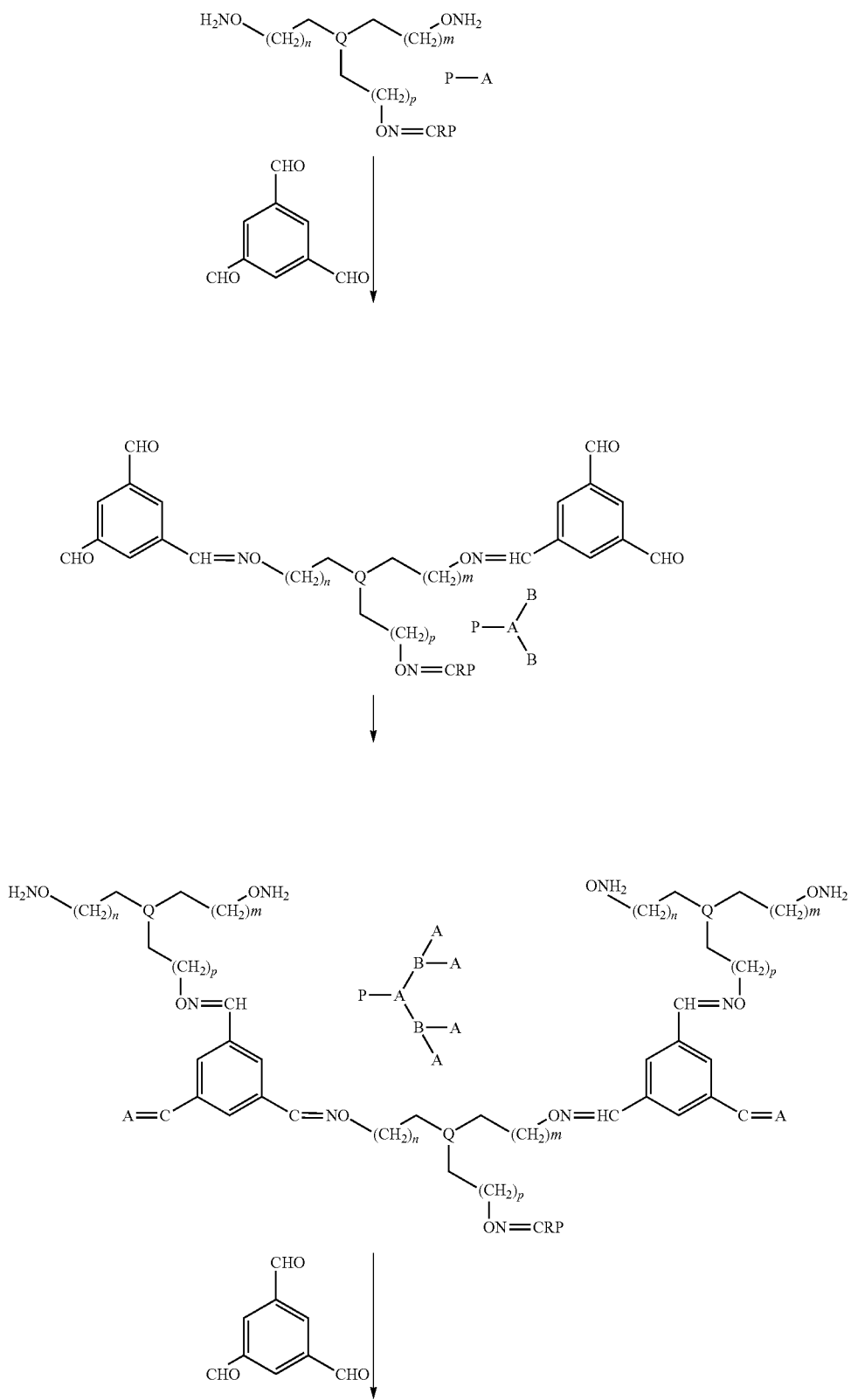
Scheme 13

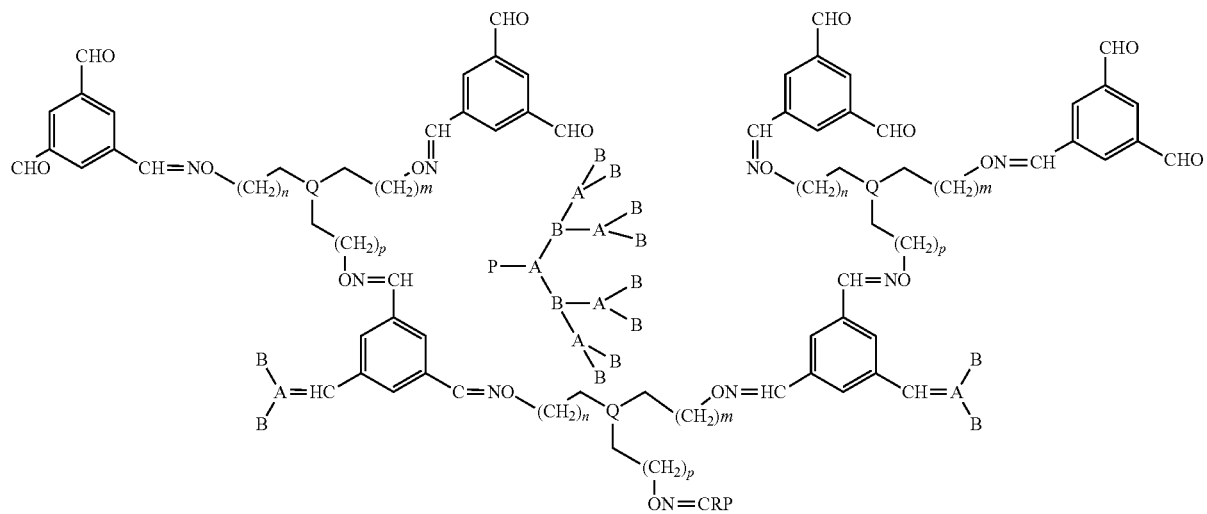

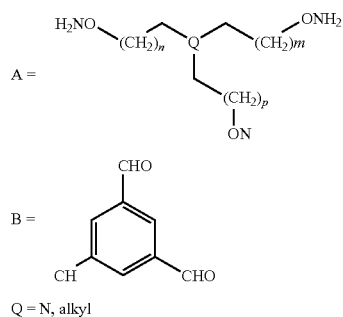

Q = N, alkyl

In some embodiments, compounds analogous to those shown in the above schemes, which multiply the A or B cargo per cycle can be generated using aminoxy and polyaminoxy-substrates with terephthaldehyde, isophthaldehyde, 1,3,5-diformylbenzene and their heterocyclic variants, as well as linear polyaldehydes. In certain embodiments, the aldehydes can include malonaldehyde, succinaldehyde and glutaraldehyde, where at least one of the aldehyde functions can be protected, for example as an acetal. (C. Botteghi and F. Soccolini, Synthesis, 592-604, 1985; C.-C. Chang, B.-S. Liao, S.-T. Liu, *Synlett*, 2007, 283-287).

Scheme 14

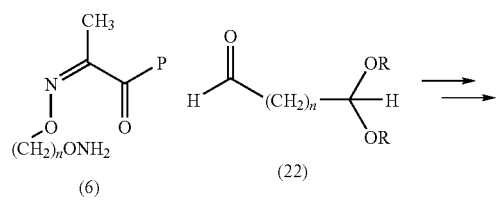

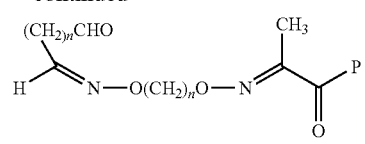

As shown in scheme 14, by varying the number of cycles and the structures of the aminoxy and aldehyde substrates, diverse polyfunctional side chains can be introduced onto protein frameworks. This coupling methodology can offer numerous advantages, such as the possibility for swiftly establishing covalent linkages and generating multivalent species.

In certain embodiments, in lieu of building towers of alternating aminoxy and carbonyl headgroups to generate multivalent species through sequential rounds of oxime formation, the desired head group functionality can be prepared independently as illustrated in scheme 15 below for the alkoxyl secondary amine. This entity can then be grafted onto the protein through oxime formation with the protein keto-amide after deprotecting the aminoxy function.

Scheme 15

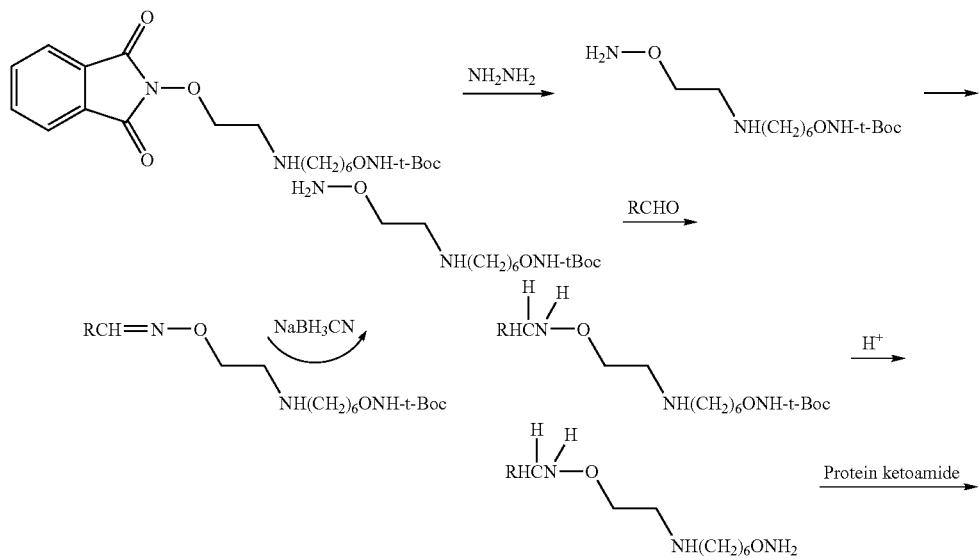

A further advantage of the present invention is that it allows for the incorporation of diverse forms of the conjugate and modifications that cannot be produced directly from the protein-oxime conjugate without sacrificing biological activity under relatively harsh reaction conditions for a protein. Another advantage is that it also provides a way to differentiate aminoxy functions by employing orthogonal protecting groups as shown in scheme 16 below.

Scheme 16

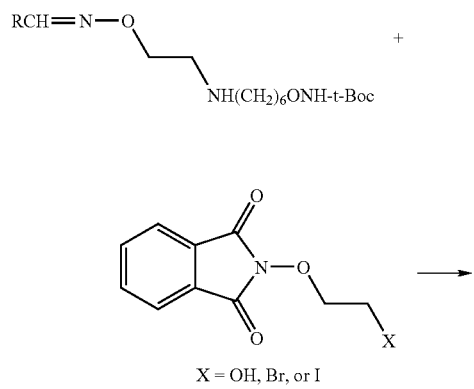

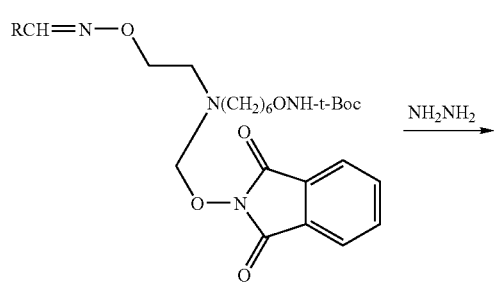

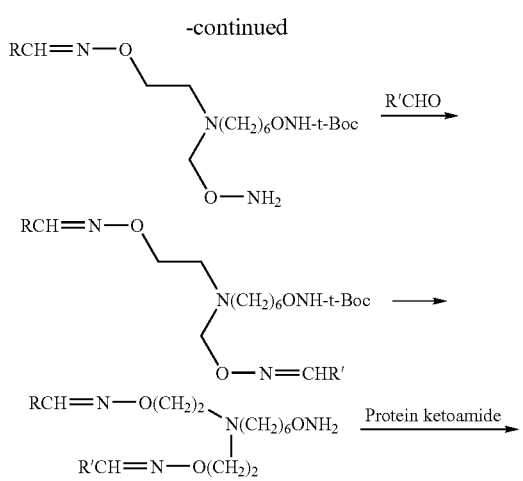

In various embodiments, the present invention provides a general method of covalently attaching to a protein such as annexin V (and other members of the annexin family) a variety of commercially useful entities. Entities such as chelated radionuclides, drugs, antibodies, optical labels, oligonucleotides and the like can be incorporated. For example, metal chelates such as NOTA and DOTA chelates of gallium and technetium can be employed as imaging agents and synthetic motifs.

Precursors to DOTA, and NOTA entities and the like can be modified for example, with appended hydrazino and aminoxy functions to allow their attachment to annexin targets, themselves modified as ketoamides, without regard to stereochemistry of the oxime linkage.

In some embodiments, the addition of mercaptoethanol or dithiothreitol to the reaction mixture containing ketoamides and O-substituted hydroxylamines, can facilitate the conversion of any residual ketoamides to the corresponding oximes. A distinctive advantage of the method is that it simplifies isolation and purification of the oxime product.

Scheme 17

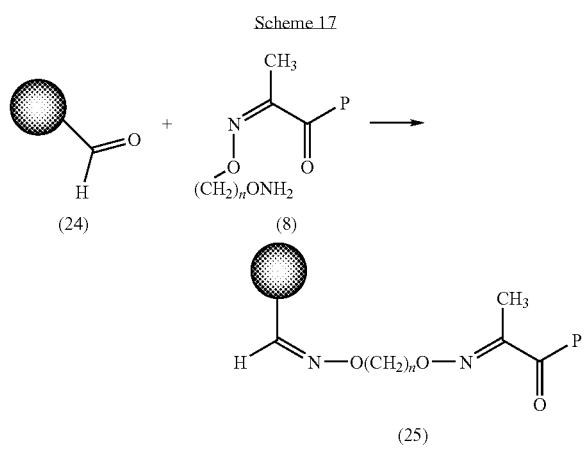

In some embodiments, as shown in scheme 17, the aminoxy group of (8) can be tethered to a solid support (24). A variety of solid supports commonly used in the art can be employed. In various embodiments, solid supports such as Agarose, styrene and Tentagel can be used. In certain embodiments the aldehyde and/or aminoxy linkers can also be used to attach dendrimers and polyfunctional entities (vide supra) to proteins and thus provide an avidity component for trapping and binding multiple ligands.

Given the rapidity of the aldehyde reactions with the N-terminally modified protein, the highly nucleophilic aminoxy function can be utilized for the introduction of aldehydes that can provide a side chain-electrophilic center. Using this methodology, various small molecule drugs can be attached to modified proteins, and various fusions of pairs of macromolecules can be prepared, i.e., combinations of protein hormones, protein therapeutics, or enzymes with each other, or with antibodies.

Scheme 18 shows an embodiment of the invention. Conjugate (15) which can be formed as shown in scheme 11 can be further reacted with ω-aminoxy-fatty acids to form the corresponding oximated fatty acid derivatives. An advantage of this method is that such derivatives can be used to enhance binding of the target proteins to carriers such as human serum albumin to extend protein lifetimes.

In another embodiment, conjugate (15) can be further reacted with compound (9) to form the corresponding (hetero- or homo-dimeric) fusion protein or fused protein via another oxime linkage. In certain embodiments, the nucleophilic and/or electrophilic moieties on the two macromolecular substrates can be interchanged to obtain two distinct adducts. For example, the nucleophilic moiety such as an alkoxylamine, hydrazine or semicarbazide on the first substrate can be reacted with the electrophilic moiety such as an aldehyde or ketone carbonyl group on a second substrate which had been derived from an aminoxy-protein condensed with a small molecule di- or poly-aldehyde. Alternatively the first substrate can analogously be converted to the aldehyde acceptor, and condensed with the aminoxy precursor of the second substrate. In some embodiments, the adduct can be formed via a hydrazone or semicarbazone linkage. An advantage of this method is that two similar or completely different peptides, polypeptides or proteins can be coupled or fused together efficiently and site-specifically to provide homogeneous and difficulty accessible adducts.

Scheme 18

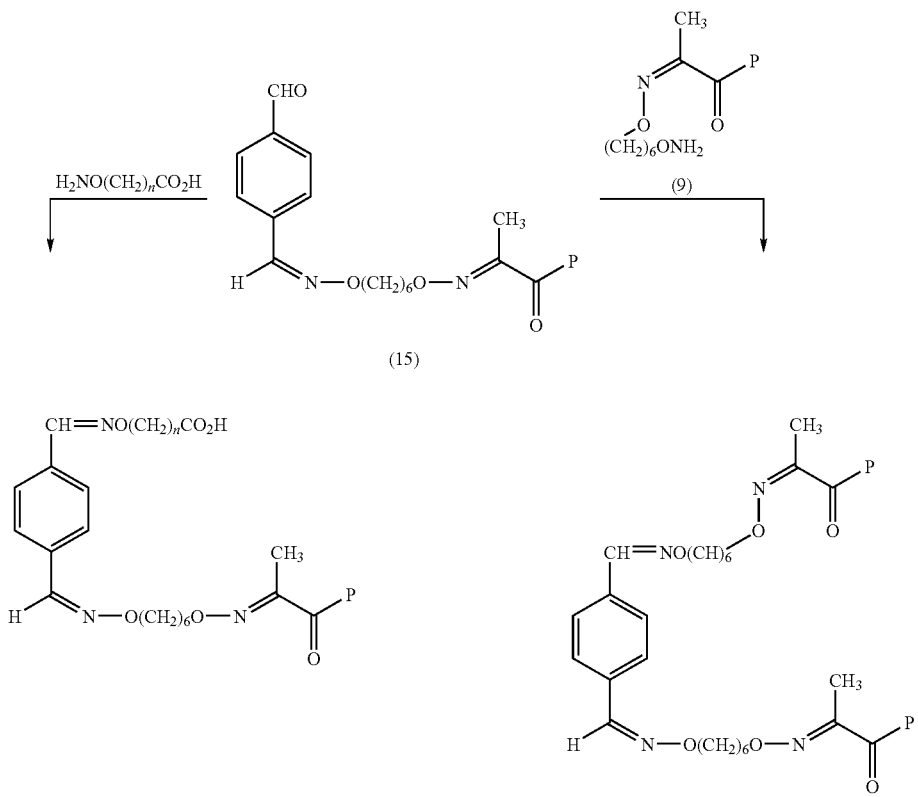

Conjugate (21) can be obtained via the steps shown in scheme 11. In some embodiments, conjugate (21) can be further reacted with, for example alkoxylamines to form the corresponding bis-oximes as shown in scheme 19. In some embodiments, conjugate 21 can be reacted with alkoxylamines, hydrazines, semicarbazides or any combination thereof to generate the corresponding oximes, hydrazones, semicarbazones or mixed linkage adducts, respectively. An advantage of this method is that the alkoxylamines, hydrazines and semicarbazides can be further coupled or fused with peptides, polypeptides and proteins containing an α-carbonyl group at the N-terminus.

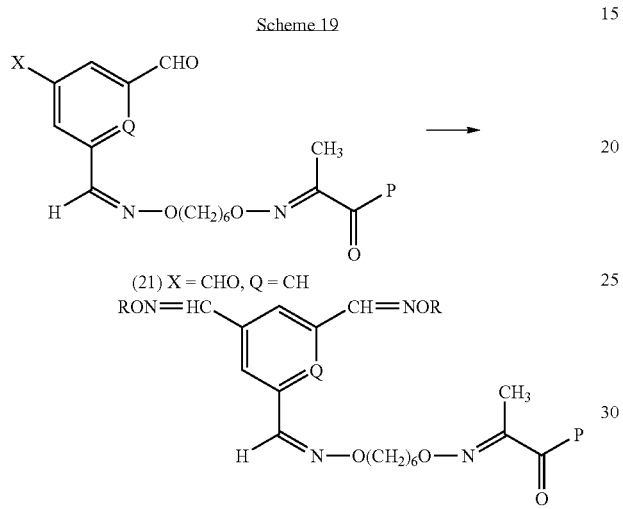

The present invention generally relates to site-specific modifications of proteins at their N-termini. In particular, the present invention relates to chemical modification of annexin and leptin proteins, substantially modified at their N-termini via highly selective transamination reactions, These transamination reactions provide a pathway to homogeneous adducts such as diverse oximino-ether derivatives, which exploit bifunctional entities capable of installing biologically useful ligands or latent reactive groups. The latter can be elaborated in sequential reactions to provide multivalent headgroups for the introduction of small molecule ligands, or coupled to proteins to provide fusion proteins, site-specifically. The present invention further relates to methods of making and using the resulting adducts in radio-labeling, molecular imaging applications, and treatment of disorders such as cancer, Crohn's disease, atherothrombosis, arthritis, and plaque rupture.

Cross-Linking of Proteins and Other Macromolecules

The cross linking of two objects such as, for example, proteins and/or other macromolecules, can have many applications for example, derivatization of cells, antibodies and diverse therapeutically, or industrially relevant proteins.

Glutaraldehyde, has been regarded as a successful cross-linking agent and studies of collagen cross-linking with dialdehydes having chain lengths of two to six carbons have shown that the reactivity in this series is—optimal at five carbons (Bowes J. H. and C. W. Cater, Biochim. Biophys. Acta 168:341-352 (1994). Glutaraldehyde is known to exist in multiple forms in aqueous solution. Many of these forms can be reactive towards entities such as, for example, amine residues. Such reactivity can create the possibility of complex, heterogeneous mixtures of products stemming from glutaraldehyde reactions with proteins (See, e.g., Migneault I, Dartiguenave C, Bertrand M J, Waldron K C, "Glutaraldehyde: behavior in aqueous solution, reaction with proteins, and application to enzyme crosslinking.", Biotechniques. 2004 37:790-6, 798-802). The tendency of aldehydes to undergo enol formation with attendant aldol condensations can be a complicating feature of glutaraldehyde coupling. The tendency can be attributable to the presence of alpha hydrogens that enable enol formation.

In some embodiments, a more advantageous approach to protein coupling can be utilized. The approach can involve the reaction of an aromatic carbonyl-alkoxylamine pair. In certain embodiments, one protein can be altered to bear a carbonyl function, and then can be contacted with another member of a pair. The other member can be altered to include an alkoxylamine. An advantage of the present invention is that an intrinsically rapid reaction in aqueous media of a carbonyl species with an aminoxy group (or other alpha nucleophile) can be utilized to couple proteins site-specifically. In various embodiments, coupling of proteins as diverse as annexin V, leptin, and myoglobin, which are modified at their N-terminals, site-specifically, can be simply accomplished.

In some embodiments, aldehydes lacking enolizable hydrogens can serve as one member of the reactive couple. Examples include terephthaldehyde, 4,4'-Bis-formylbiphenyl, 4-(4-formylphenoxy)-benzaldehyde and 2,2'-bipyridine-5,5'-dicarbaldehyde, and bis-phenoxy-alkanes, as well as the latter's polyethylene glycol-chain analogs shown below.

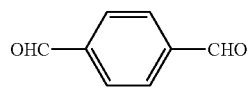

Advantages of the present invention is that di-aldehyde linkers such as the terephthaldehyde above, are (1) not in equilibrium with numerous potentially reactive species, (2) are quite stable in aqueous media, and (3) can undergo coupling reactions site specifically with the aminoxy-proteins of this invention.to provide the corresponding oximes. What is more, the coupling reactions can be accelerated by catalysis by simple amines such as ethylene diamine and aniline.

In small molecule reactions between alkoxylamines and di-carbonyl species the immediate product, the oxime-aldehyde can compete with the di-carbonyl substrate starting material for oxime formation. An advantage of the present invention is that the mono-aldehyde adduct formed between the di-aldehyde and the aminoxy-protein can be the quantitatively formed end-product. Further conversion to the bis-oxime protein dimer can be suppressed or minimal because of the difficulty of bringing together two large proteins at low concentration, in competition with the reaction of a large excess of small molecule di-aldehyde substrate with alkoxylamine. The mono-aldehyde form of the protein can be separated from small molecule substrates by conventional techniques and is then available as an intermediate for site-specific homo- or hetero-dimer formation.

In certain embodiments, after standing in only buffer over periods of several minutes to days, benzaldehyde moieties tethered to proteins can react with small molecule alkoxylamines. An advantage of the present invention is that the reactivity of tethered benzaldehyde functions on the protein surface can be directed towards external nucleophiles such as alkoxylamines in the presence of the protein's amino acid side chains such as, for example, lysine amino and other nucleophilic groups of proteins.

The cross-linking reaction using aromatic aldehyde motifs can be further extended by linking an aromatic aldehyde to another entity for example, a maleimide component. Maleimide components can preferentially react with cysteine thiols (Kim Y, Ho S O, Gassman N R, Korlann Y, Landorf E V, Collart F R, Weiss S., "Efficient site-specific labeling of proteins via cysteines.", Bioconjug Chem. 2008 19:786-91.)

The combination of maleimide and aromatic aldehyde in reagents such as, for example, the structures shown below, can enormously expand the candidate possibilities for protein coupling. The potential targets include a variety of proteins with natural primary amino acid sequences that contain a single cysteine residue (such as annexin V) as well as numerous recombinant proteins in which cysteines can be engineered for conjugation purposes.

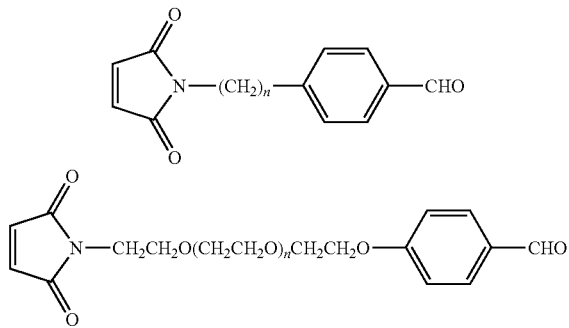

Methods of Use
Methods of Treatment and Methods of Use as Diagnostics

The compounds of the present invention, i.e., N-terminus modified proteins can be used in a variety of applications such as screening, diagnostic detection, and/or as pharmaceutical formulations to treat disorders such as cancer, atherothrombosis, Crohn's disease, plaque rupture and arthritis.

A skilled artisan appreciates the variety of applications for proteins such as granulocyte macrophage colony-stimulating factor, human superoxide dismutase, annexin and leptin fused with either other proteins or radioactive nuclides such as fluorobenzaldehyde for use in screening or detection of apoptosis. In particular the known methods and techniques as discussed in the following references can be employed and are herein incorporated by reference.

Annexins are a group of calcium-binding structural proteins that play a role in the regulation of membrane trafficking, cellular adhesion, and cell signaling. See, "Annexins: Molecular Structure to Cellular Function", Ed. Barbara A. Seaton, Landes Bioscience, 1996. They are a structurally conserved family of proteins characterized by reversible $Ca^{2+}$-dependent intracellular membrane binding. Annexins associate to membranes for their proposed functions which include vesicle trafficking, membrane fusion and ion channel formation. High-resolution crystal structures of the soluble forms of several annexins are available. These proteins bind to surfaces of phosphatidylserine-containing phospholipid bilayers either in the presence of $Ca^{2+}$ or under conditions of low pH (pH 5-6).

There are at least 10 distinct annexins in vertebrates (annexins I-VIII, XI and XIII) and a number of them, based on their pharmacological properties, possess high therapeutic potential in humans as well as provide a basis for the construction of various imaging agents as diagnostic tools and products. See, "Annexinopathies.", Subcell Biochem. 2007; 45:1-28, Hayes M J, Longbottom R E, Evans M A, Moss S E; "Annexin-A1: a pivotal regulator of the innate and adaptive immune systems", Br J. Pharmacol. 2008 September; 155(2):152-69., D'Acquisto F, Perretti M, Flower R J.; "Annexin-1 modulates repair of gastric mucosal injury", Am J Physiol Gastrointest Liver Physiol 294: G764-G769, 2008. Gary R. Martin, Mauro Perretti, Roderick J. Flower, and John L. Wallace; "Annexin Alin the brain-undiscovered roles?" Trends Pharmacol Sci. 2008 March; 29(3):135-42, Solito E, McArthur S, Christian H, Gavins F, Buckingham J C, Gillies G E; "Annexin A5: shifting from a diagnostic towards a therapeutic realm." Cell Mol Life Sci. 2007 64(22):2859-62. Kenis H, Hofstra L, Reutelingsperger C P. Annexin IV: "Placental anticoagulant proteins: isolation and comparative characterization four members of the lipocortin family.", Tait J. F., Sakata M., McMullen B. A., Miao C. H., Funakoshi T., Hendrickson L. E., Fujikawa K.; Biochemistry 27:6268-6276 (1988); Annexin VI: "Structure and expression of cDNA for calphobindin II, a human placental coagulation inhibitor.", Iwasaki A., Suda M., Watanabe M., Nakao H., Hattori Y., Nagoya T., Saino Y., Shidara Y., Maki M., J. Biochem. 106:43-49 (1989); Annexin VIII: "Vascular anticoagulant beta: a novel human Ca2+/phospholipid binding protein that inhibits coagulation and phospholipase A2 activity. Its molecular cloning, expression and comparison with VAC-alpha.", Hauptmann R., Maurer-Fogy I., Krystek E., Bodo G., Andree H., Reutelingsperger C. P. M.

The present invention relates to annexin derivatives. As used herein, the term "annexin" refers to a class of proteins characterized by their ability to bind with high affinity to membrane lipids in the presence of millimolar concentrations of calcium. Annexins have been shown to exhibit anticoagulatory effects that are mediated by the binding of annexins to negatively charged surface phospholipids (e.g., on activated platelets). Annexin V is a representative annexin molecule used in the description of the present invention. Annexins within the scope of the invention include annexins I, II, III, IV, V, VI, VII, VIII, XI, XIII, XXXI, and XXXII. The term "annexin" includes native annexin purified from natural sources such as, for example, human placenta, or annexin molecules containing a native sequence produced through genetic engineering, recombinant, or other means. The term "annexin" includes modified annexins as defined below, derived from or produced by any source. As used herein, the term "modified annexin" refers to an annexin molecule wherein the native sequence or molecule is altered in such a way without materially altering the membrane binding affinity of the annexin. Such annexins can be produced by chemical, genetic engineering, or recombinant techniques. The modification can include sequence modification through the addition of several amino acid residues, and/or an addition/deletion of an amino acid at a single site on the native or genetically engineered sequence. In the context of the present invention, modified annexins include annexins modified at the N-terminus by the addition of amino acid residues.

The present invention further relates to leptin derivatives and analogs, including leptin fusion proteins, leptin muteins, leptin receptor agonists, or active fragments or fractions thereof, and salts of all of same, and pharmaceutical compositions containing leptin, leptin fusion proteins, leptin muteins, leptin receptor agonists, active fractions thereof, or salts of all of same.

As used herein the term "leptin" refers to naturally available leptin, commercially available leptin, analogs of leptin, in which one or more of the amino acid residues are replaced by different amino acid residues, or are deleted, or one or more amino acid residues are added to the original sequence of leptin without changing considerably the activity of the resulting products as compared with wild type leptin or its active fragments or fractions. The leptins used in the present invention can be prepared by known synthesis and/or by site-directed mutagenesis techniques, or any other known technique as appropriate.

Any such leptin preferably has a sequence of amino acids sufficiently duplicative of that of natural leptin such as to have substantially similar activity to leptin or its active fragments or fractions. Thus, it can be determined whether any given leptin has substantially the same activity as natural leptin by means of routine experimentation comprising subjecting such a leptin, e.g., to a simple cell proliferation assay, as a leptin which blocks cell proliferation retains sufficient activity of leptin and therefore has at least one of the disclosed utilities of leptin and thus has substantially similar activity thereto.

In at least one preferred embodiment, any such leptin has at least 40% identity or homology with the sequence of one of the leptins. More preferably, it has at least 50%, at least 60%, at least 70%, at least 80% or, most preferably, at least 90% identity or homology thereto.

A variety of polypeptides or proteins not specifically described herein my be used within the scope of the methods and compositions herein. Such polypeptides include those described in U.S. Pat. No. 7,534,866, which is incorporated herein by reference in its entirety. Apoptosis is a genetically defined cell death that involves activation of a core enzymatic machine consisting of cysteine proteases, called caspases. An early molecular event in apoptosis is the flipping of phosphatidylserine (PS) from the inner lipid bilayer to the outer layer of the plasma membrane. Annexin V binds PS with extremely high affinity (Kd=7 nmol/L), as well as specificity, and has been used in vitro to identify apoptotic cells.

Annexin V labeled with a positron emitter such as $^{18}$F has been found to be capable of detecting tumor cell death, thereby serving as an early predictor of clinical response to anti-tumor therapy. See e.g. US Patent Publication No. 20070031333 which is incorporated herein by reference in its entirety. It is believed that the inherent advantages of PET make $^{18}$F-Annexin V a better imaging agent than other such agents used in the art for quantifying the amount of cell death in tumors, especially in small metastatic lesions.

The increased risk of mortality due to cardiovascular diseases, such as atherothrombosis and plaque rupture, specifically in systemic lupus erythematosus (SLE) patients, is a major clinical problem. Cardiovascular diseases in SLE patients is associated with both traditional risk factors like dyslipidemia, and non-traditional risk factors including increased oxidation of low density lipoprotein (oxLDL), raised activity in the tumour necrosis factor (TNF)-system (closely associated with dyslipidemia), systemic inflammation as determined by CRP, homocystein and anti-phospholipid antibodies. Anti-phospholipid may cause the anti-phospholipid antibody syndrome (APS), common in SLE patients and characterized by recurrent pregnancy loss and recurrent thrombosis. Different forms of anti-phospholipids have also been implicated in cardiovascular diseases in the general population. See US Patent Publication No. 20080044404 which is incorporated herein by reference in its entirety. In some embodiments, Annexin V or an N-terminal fragment of Annexin V can be administered according to the invention, and can bind to the endothelial plaque on a first passage. For example, a composition for injection comprising Annexin V or an N-terminal fragment of Annexin V with or without additives can prevent atherothrombosis by stabilizing the carotid plaque through an instant binding.

Many gastrointestinal disorders, such as peptic ulcers, gastritis, ulcerative colitis and Crohn's disease, are characterized by symptoms that include severe abdominal pain, cramps, fever, diarrhea, anemia, and weight loss. Crohn's disease is an autoimmune disorder that appears to enter an acute phase in response to stress, and its ulcerous lesions are particularly active in forming adhesions that must be removed surgically. At present, there are no specific therapies for this disorder. In certain embodiments, the compounds of the present invention can be used for the treatment of Crohn's disease.

Compounds of the present invention can be used for the treatment of cancer, where the cancer is selected from the group consisting of multiple myeloma, chronic myelogenous leukemia, pancreatic cancer, non-small cell lung cancer, lung cancer, breast cancer, colon cancer, ovarian cancer, prostate cancer, malignant melanoma, non-melanoma skin cancers, gastrointestinal stromal tumors, hematologic tumors, hematologic malignancies, childhood leukemia, childhood lymphomas, multiple myeloma, Hodgkin's disease, lymphomas of lymphocytic origin, lymphomas of cutaneous origin, acute leukemia, chronic leukemia, acute lymphoblastic leukemia, acute myelocytic leukemia, chronic myelocytic leukemia, plasma cell neoplasm, lymphoid neoplasm and cancers associated with AIDS.

In one example, the compounds of the present invention can be utilized to prepare fusion proteins. The genetic combination of originally separate proteins, fusion proteins are successful biopharmaceuticals. Curr Opin Drug Discov Devel. 2009 March; 12(2):284-95. Fusion-proteins as biopharmaceuticals—applications and challenges. Schmidt SR. The fusion proteins that are approved for use in the clinic and those that are currently in clinical trials are summarized therein. Fusion proteins can be categorized into several groups according to their features. In the first group, effector molecules are fused to Fc domains, albumin or transferrin to extend the plasma half-life of the fusion product. In the second group, toxicity is conveyed by fusion proteins to toxins, enzymes or cytokines. The third application utilizes fusion partners to enable novel delivery and targeting routes. In some embodiments, the compounds of the invention can contain an aldehyde or an aminoxy linker. Such linkers can be utilized to attach a variety of proteins thereby forming the corresponding fusion proteins.

Site-specific $^{18}$F-labeling of the protein hormone leptin using a general two-step ligation procedure is described in J Am Chem. Soc. 2008 Jul. 16; 130(28):9106-12. Epub 2008 Jun. Flavell R R, Kothari P, Bar-Dagan M, Synan M, Vallabhajosula S, Friedman J M, Muir T W, Ceccarini G. The protein hormone leptin acts to regulate body fat and energy expenditure. Resistance to this hormone is implicated in human obesity and its pathophysiological consequences. In order to gain insight into the mechanism of leptin resistance, an $^{18}$F-labeled derivative was developed to study the biodistribution of the hormone using positron emission tomography (PET). The modified hormone was shown to be biologically active in vitro and in vivo, and it was applied to PET imaging in ob/ob mice i.e., mice with mutations on both ob genes. These protocols will allow for use in PET imaging in systems from mouse to man. Accordingly, the N-terminus modified proteins described herein could be radiolabeled to gain insight into protein function.

Mol Imaging Biol. 2008 July-August; 10(4):177-81. Epub 2008 May. Direct site-specific radiolabeling of an affibody protein with 4-[$^{18}$F] fluorobenzaldehyde via oxime chemistry. Namavari M, Padilla De Jesus O, Cheng Z, De A, Kovacs E, Levi J, Zhang R, Hoerner J K, Grade H, Syud F A, Gambhir S S. A methodology for preparing $^{18}$F-labeled affibody protein, specifically $^{18}$F-Anti-HER2 dimeric affibody (14 kDa), for in vivo imaging of HER2neu with positron emission tomography (PET) was described in the following study. Aminooxy-functionalized affibody (Anti-HER2-ONH2) was incubated with 4-[$^{18}$F]fluorobenzaldehyde in ammonium acetate buffer at pH 4 in the presence of methanol at 70 degrees C. for 15 min. The resulting $^{18}$F-labeled affibody molecule was evaluated as a PET probe in xenograft models expressing HER2. Accordingly, the N-terminus modified proteins described herein can be utilized in preparing $^{18}$F labeled radionuclides with further applications in PET.

Antitumor treatment by means of fluorescence molecular tomography with an annexin V-Cy5.5 conjugate is described in Ntziachristos V, Schellenberger E A, Ripoll J, Yessayan D, Graves E, Bogdanov A Jr, Josephson L, Weissleder R. Proc Natl Acad Sci USA. 2004 Aug. 17; 101(33):12294-9. Epub 2004 August 10. Surface-functionalized nanoparticle library yields probes for apoptotic cells and Schellenberger E A, Reynolds F, Weissleder R, Josephson L. Chembiochem. 2004 Mar. 5; 5(3):275-9. Optimal modification of annexin V with fluorescent dyes. Schellenberger E A, Weissleder R, Josephson L. Chembiochem. 2004 Mar. 5; 5(3):271-4. Accordingly, the N-terminus modified proteins described herein can be utilized in fluorescence molecular tomography with further applications in antitumor treatment.

In "Annexin V-CLIO: a nanoparticle for detecting apoptosis by MRI", Schellenberger E A, Bogdanov A Jr, Högemann D, Tait J, Weissleder R, Josephson L. Massachusetts General Hospital, Charlestown, Mass., USA, have conjugated Annexin V, which recognizes the phosphatidylserine of apoptotic cells, to crosslinked iron oxide (CLIO) nanoparticles, a functionalized superparamagnetic preparation developed for target-specific magnetic resonance imaging (MRI). The resulting nanoparticle had an average of 2.7 annexin V proteins linked per CLIO nanoparticle through disulfide bonds. Using camptothecin to induce apoptosis, a mixture of Jurkat T cells (69% healthy and 31% apoptotic) was incubated with annexin V-CLIO and was applied to magnetic columns. In a phantom MRI experiment, untreated control cells (12% apoptotic cells, 88% healthy cells) and camptothecin-treated cells (65% apoptotic cells, 35% healthy cells) were incubated with either annexin V-CLIO (1.0, 0.5, and 0.1 microgram Fe/mL) or with unlabeled CLIO. Conjugation of annexin V to CLIO affords a strategy for the development of a MRI imaging probe for detecting apoptosis. Accordingly, the N-terminus modified proteins described herein can be utilized in the preparation of agents/probes that can be utilized in MRI.

In "Magnetic resonance imaging of cardiomyocyte apoptosis with a novel magneto-optical nanoparticle" Magn Reson Med. 2005 September; 54(3):718-24, Sosnovik D E, Schellenberger E A, Nahrendorf M, Novikov M S, Matsui T, Dai G, Reynolds F, Grazette L, Rosenzweig A, Weissleder R, Josephson L describe that the ability to image cardiomyocyte apoptosis in vivo with high-resolution MRI could facilitate the development of novel cardioprotective therapies. The sensitivity of the novel nanoparticle AnxCLIO-Cy5.5 for cardiomyocyte apoptosis was compared in vitro to that of annexin V-FITC and showed a high degree of colocalization. MRI was then performed, following transient coronary artery (LAD) occlusion, in five mice given AnxCLIO-Cy5.5 and in four mice given an identical dose (2 mg Fe/kg) of CLIO-Cy5.5. MR signal intensity and myocardial T2* were evaluated, in vivo, in hypokinetic regions of myocardium in the LAD distribution. Ex vivo fluorescence imaging was performed to confirm the in vivo findings. Accordingly, the N-terminus modified proteins described herein can be utilized in the preparation of agents/probes that can be utilized in fluorescence imaging and MRI.

US 20060275834 describes using fluorescently labeled annexin proteins in survival assays for treatment of Crohn's disease. US 20080200385 describes using annexin proteins in diagnosis of intestinal cancers. US 20080044404 describes the use of native Annexin V or an N-terminal fragment as an active component or a subfraction of immunoglobulins to manufacture a pharmaceutical composition to improve or increase the Annexin V-binding to carotid plaque for preventing atherothrombosis. US 20030166532 describes using a modified annexin to remain in circulation for sufficient time to provide a sustained therapeutic effect for the treatment of thrombosis. The methods described in the above mentioned publications can also be employed using the compounds of the present invention and are herein incorporated by reference.

Diagnostics

The compounds described herein can be used as targeting molecules in radiopharmaceutical formulations of the invention. In some embodiments, the compounds of the present invention can be used as imaging agents. These imaging agents bind to, complex with or react with the target sought to be bound or localized to.

The labeled compounds can be used in connection with methods for imaging an internal region of a patient and/or diagnosing the presence or absence of a disease in a patient by the application and/or detection of an energy source. Exemplary imaging agents include contrast agents for use in connection with ultrasound, magnetic resonance imaging, radionuclide imaging, or x-ray (including computed tomography) imaging of a patient, and the compositions described herein.

A positron, i.e. positive electron, emitted from a positron-emitting source disappears to produce a pair of gamma rays, i.e. annihilation radiation. In positron tomography, the pair of .γ rays is converted into electrons, and the electrons are counted in real time by a detector. Devices for use in such positron tomography are known in the art. The positron tomography enables the measurement of the distribution and accumulated concentration of the positron-emitting source and thus is used to diagnose some diseases.

Specifically, for example, $^{18}$F-labeled fluorodeoxyglucose administered into the body is more taken up by cancer cells, because cancer cells divide more rapidly than normal cells and need more glucose. When this state is imaged using a positron tomograph, the distribution and accumulated concentration of the fluorodeoxyglucose can be measured so that the presence or absence and the size of the cancer lesion can be determined. Further, positron tomography can reveal that administered $^{18}$F-fluorodeoxyglucose is more concentrated in the brain, since brain cells also consume more energy than other cells. When brain cells are partially damaged for some reason, the uptake of glucose into the damaged part may decrease. Therefore, the presence or absence of brain dysfunction can be diagnosed by positron tomography. Consequently, positron tomography is applicable to the diagnosis of diseases and thus greatly expected to undergo further development in the future.

Magnetic resonance imaging (MRI) can be used for producing cross-sectional images of the body in a variety of scanning planes, e.g., axial, coronal, sagittal or orthogonal without exposure to radiation. MRI employs a magnetic field, radio frequency energy and magnetic field gradients to make images of the body. The contrast or signal intensity differences between tissues mainly reflect the TI (longitudinal) and T2 (transverse) relaxation values and the proton density, which generally corresponds to the free water content, of the tissues. The T1 and T2 relaxation rates can be altered by the presence of a paramagnetic ion, for example Gd, Fe, or Cu.

MRI generally requires the use of contrast agents to assist in differentiation of the tissue of interest from the surrounding tissues in the resulting image. In the past, attention has focused primarily on paramagnetic contrast agents for MRI. Paramagnetic contrast agents involve materials which contain unpaired electrons. The unpaired electrons act as small magnets within the main magnetic field to increase the rate of longitudinal (T1) and transverse (T2) relaxation. Paramagnetic contrast agents typically comprise metal ions such as transition metal ions, which provide a source of unpaired electrons. However, since these metal ions are also generally highly toxic, the ions are typically chelated.

Ultrasound is another valuable diagnostic imaging technique and provides certain advantages over other diagnostic techniques. Ultrasound involves the exposure of a patient to sound waves. Generally, the sound waves dissipate due to absorption by body tissue, penetrate through the tissue or reflect off of the tissue. The reflection of sound waves off of tissue, generally referred to as backscatter or reflectivity, forms the basis for developing an ultrasound image. In this connection, sound waves reflect differentially from different body tissues. This differential reflection is due to various factors, including the constituents and the density of the particular tissue being observed. Ultrasound involves the detection of the differentially reflected waves, generally with a transducer that can detect sound waves having a frequency of one megahertz (mHz) to ten mHz. The detected waves can be integrated into an image which is quantitated and the quantitated waves converted into an image of the tissue being studied. Ultrasound also generally involves the use of contrast agents such as suspensions of solid particles, emulsified liquid droplets, and gas-filled bubbles or vesicles.

The imaging agents of the present invention can be adapted for use in the aforementioned imaging and diagnostic techniques for the imaging and/or detection of a variety of diseases and disorders in vivo. Such diseases include cancer, arthritis, atherothrombosis, plaque rupture, and Crohn's disease.

In another embodiment, the imaging agents of the present invention can be adapted for use in the aforementioned imaging and diagnostic techniques for the imaging and/or detection of cancer.

In still other embodiments, the imaging agents of the present invention can be adapted for use in the aforementioned imaging and diagnostic techniques for the imaging and/or detection of diseases and disorders related to the skin, heart, muscles, eyes, ears, tongue, lungs, and bones of a subject.

In still another embodiment, the imaging agents of the present invention can be adapted for use in the aforementioned imaging and diagnostic techniques for in vitro imaging. For example, the compounds can be used for in vitro imaging of tissue samples, such as human tissue samples. The tissue samples can be healthy or diseased. The tissue samples may, for example, result from a biopsy or autopsy.

Pharmaceutical Compositions

The compounds of the present invention are suitable as active agents in pharmaceutical compositions that are efficacious particularly for treating disorders such as cancer, arthritis, atherothrombosis, plaque rupture and Crohn's disease. The pharmaceutical composition in various embodiments has a pharmaceutically effective amount of the present active agent along with other pharmaceutically acceptable excipients, carriers, fillers, diluents and the like.

As used herein, a "pharmaceutically effective amount" of the compound is that amount necessary or sufficient to treat or prevent a disorder, and/or a disease or condition described herein. In an example, an effective amount of a compound of the invention is the amount sufficient to treat a disorder in a subject. The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. A compound of the invention can be administered to the subject either prior to or after the onset of a disorder. Further, several divided dosages, as well as staggered dosages can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

A typical formulation can be prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations can be prepared using conventional dissolution and mixing procedures. For example, the bulk drug substance (i.e., compound of the present invention or stabilized form of the compound, such as a complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) can be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container can also include a tamper-proof assemblage to prevent indiscreet access to the contents of the package. In addition, the container has deposited thereon a label that describes the contents of the container. The label can also include appropriate warnings.

Pharmaceutical, formulations of therapeutic compounds of the invention can be prepared for various routes and types of administration. A compound having the desired degree of purity can be optionally mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation can be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 can be a suitable embodiment.

The compound for use herein is preferably sterile. The compound ordinarily will be stored as a solid composition, although lyophilized formulations or aqueous solutions are acceptable.

The pharmaceutical compositions of the invention will be formulated, dosed, and administered in a fashion, i.e. amounts, concentrations, schedules, course, vehicles, and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

In some embodiments, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients, and stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). The compounds of the present invention can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations can be prepared. Suitable examples of sustained-release preparations include semipermeable matrices of solid hydrophobic polymers containing the compound(s), which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid.

The formulations to be used for in vivo administration can be sterile, which can be accomplished by filtration through sterile filtration membranes.

The formulations include those suitable for the administration routes detailed herein. The formulations may conveniently be presented in unit dosage form and can be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations can be prepared by uniformly and intimately bringing into association the active ingredient with liquid carriers or finely divided solid carriers or both, and then, if necessary, shaping the product.

Formulations of the compounds suitable for oral administration can be prepared as discrete units such as pills, capsules, cachets or tablets each containing a predetermined amount of the compounds.

Compressed tablets can be prepared by compressing in a suitable machine the active ingredient in a free-flowing form such as a powder or granules, optionally mixed with a binder, lubricant, inert diluent, preservative, surface active or dispersing agent. Molded tablets can be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g. gelatin capsules, syrups or elixirs can be prepared for oral use. Formulations of a compound intended for oral use can be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients can be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets can be uncoated or can be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax can be employed.

The formulations can be applied as a topical ointment or cream containing the active ingredient(s) in an amount of, for example, 0.075 to 20% w/w. When formulated in an ointment, the active ingredients can be employed with either a paraffinic or a water-miscible ointment base. Alternatively, the active ingredients can be formulated in a cream with an oil-in-water cream base.

If desired, the aqueous phase of the cream base may include a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention can be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both, an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of the invention contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension can also contain one or more preservatives such as ethyl or n-propyl p-hydroxy-benzoate, one or more coloring agents, one or more flavoring agents and one or more sweetening agents, such as sucrose or saccharin.

The pharmaceutical composition of a compound can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butane-diol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500.mu.g of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration can be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration can be prepared according to conventional methods and can be delivered with other therapeutic agents such as compounds heretofore used in the treatment or prophylaxis. Formulations suitable for vaginal administration can be presented as pessaries, tampons, creams, gels, pastes, foams or spray formulations containing in addition to the active ingredient such carriers as are known in the art to be appropriate.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

While it is possible for a compound of the present invention to be administered alone, it is preferable to administer the compound as a pharmaceutical composition.

Advantageously, the present invention also provides kits for use by a consumer for treating disease. The invention also provides kits for use by health providers, hospital staff and technicians. For example, the invention provides kits for using the modified proteins of the invention for diagnostic applications such as imaging. The kits can comprise a) a pharmaceutical composition comprising a compound of formula I and a pharmaceutically acceptable carrier, vehicle or diluent; and, optionally, b) instructions describing a method of using the pharmaceutical composition for treating the specific disorder. The instructions may also indicate that the kit is for treating disorder while substantially reducing the concomitant liability of adverse effects associated with administration of the composition. In certain embodiments the kits can comprise (i) a compound of structure 8, with instructions for mixing with (ii) another compound, to generate the target reagent, or active agent A "kit" as used in the instant application includes a container for containing the separate unit dosage forms such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a written memory aid, where the written memory aid is of the type containing information and/or instructions for the physician, pharmacist or subject, e.g., in the form of numbers next to the tablets or capsules whereby the numbers correspond with the days of the regimen which the tablets or capsules so specified should be ingested or a card which contains the same type of information. Another example of such a memory aid is a calendar printed on the card e.g., as follows "First Week, Monday, Tuesday," . . . etc. . . . "Second Week, Monday, Tuesday, . . . ," etc. Other variations of memory aids will be readily apparent. A "daily dose" can be a single tablet or capsule or several tablets or capsules to be taken on a given day.

Another specific embodiment of a kit is a dispenser designed to dispense the daily doses one at a time. Preferably, the dispenser is equipped with a memory-aid, so as to further facilitate compliance with the regimen. An example of such a memory-aid is a mechanical counter, which indicates the number of daily doses that, has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The following examples illustrate the preparation of certain specific compounds according to the present technology. A skilled artisan appreciates that the invention is not limited to the exemplary work described or to the specific details set forth in the examples.

EXAMPLES

Protocols for Transamination-Related Reactions

Reaction Between Protein and PLP to Produce Transaminated Protein with N-Terminal Aldoamide or Ketoamide.

Protein (concentration used can be varied from a few µg/ml to a few mg/ml) was incubated with 10 mM PLP, in 25 mM PBS, pH 6.5, at 37° C. for certain time. For annexin V, the incubation time is 4 hr. For leptin or myoglobin, the incubation time is 16 hr.

After the incubation, the sample was subject to centrifuge filtration to remove excess PLP from the solution.

Reaction Between Annexin V-Ketoamide and NOTA Aminooxy Compound (6), Scheme 7.

Annexin V-ketoamide was incubated with 100 mM of the aminoxy NOTA compound (6) at room temp for 16 hr and the reaction mixture was constantly shaken. After the incubation, the sample was subject to centrifuge filtration to remove excess NOTA aminooxy compound (6) from the solution.

Reaction Between a Protein Aldoamide/Ketoamide with Bis-Aminooxy Compounds to Produce N-Terminal Aminoxyprotein Oximes (8) Scheme 8.

The transaminated protein (aldoamide or ketoamide) was incubated with 100 mM bis-aminooxy compound (8, n=4-8) at room temp for 4 to 16 hr and the reaction mixture was constantly shaken. Upon terminating the incubation, the sample was subject to centrifuge filtration to remove unreacted bis-aminooxy starting material from the solution.

Reaction Between an Aminoxy-Protein Oximes (8, Exemplified by (9) and 4-fluorobenzaldehyde (10) Scheme 9.

Aminoxyannexin V (9), obtained as described above was incubated with 1 mM 4-fluorobenzaldehyde (10) at room temp for 10 min, pH 6.5, 25 mM PBS. The reaction is complete within 10 min. The presence of aniline or ethylene diamine accelerates the reaction. The reaction mixture was then subject to centrifuge filtration to remove excess 4-fluorobenzaldehyde from the solution.

Reaction Between Aminoxyannexin V Oximes (8), Exemplified by (9) and Di- and Tri-Aldehydes to Produce Aryl Aldehyde-Protein Bis-Oxime Products (Scheme 11)

Aminoxy annexin V oxime (9) was incubated with 1 mM polyaldehyde compounds (exemplified by terephthaldehyde (14), isophthaldehyde (16), 2,6-diformylpyridine (17) and 1,3,5-triformylbenzene (18) at room temp for 10 min at pH 6.5 and in 25 mM PBS The reaction to form the monoaldoxime with the protein species is complete within 10 min. Only one of the two or three aldehyde groups of the polyaldehyde substrates is consumed. This phenomenology is a consequence of the much lower rates of competing reactions: reaction of aminoxyproteins with newly formed aldehyde-proteins and the reaction of protein nucleophiles and aldehydes at pH 6.5. The presence of aniline can further accelerate the rate. The reaction mixture was then subject to centrifuge filtration to remove excess di-aldehyde or tri-aldehyde starting material. This procedure thus constitutes a method for introducing aldehydes onto a protein framework enabling further modification, and reverses the polarity of the protein for organic chemical reactivity.

Coupling of Aminoxyproteins (8) and Protein Aldehydes (15) and (19).

Aminoxy-protein (9) and protein aldehydes (exemplified by (15) and (19) was mixed in a molar ratio of 1 to 1. The mixture was incubated at room temp for 16 hr at pH 6.5, and 25 mM PBS, with or without the presence of 50 mM aniline and the mixture was constantly shaken. The protein-protein conjugate can easily be detected by mass spectrometry. The presence of aniline accelerates the reaction and thus leads to greater conversion to coupled product.

Reaction Between Aminoxyprotein (9) and 1,3,5-Triformylbenzene (18).

Aminoxy protein (9) was incubated with 1 mM 1,3,5-triformylbenzene (18) at room temp for 10 min as above. The reaction is complete within 10 min without catalysis. The protein di-aldehyde product (21) was then purified from excess tri-aldehyde by centrifuge filtration.

Reaction Between Protein-Aldehydes (15), (19) and (21) and Aminooxy Substrates

Protein-aldehyde (15) or (19) or protein di-aldehyde (21) products as described above were incubated with 1 mM aminooxy compounds exemplified by 5-O-aminoxypentanoic acid at room temp as above with or without the presence of 50 mM aniline. Without aniline, the reaction takes 1-2 hr to reach completion, whereas in the presence of aniline, the reaction is complete within 10 min. The final product from the reaction can be purified by centrifuge filtration. The success of this reaction demonstrates that proteins with extended frameworks terminating with aldehyde functions are capable of undergoing facile chemical reactions with nitrogen nucleophiles.

Protocols for Chemical Modification of Transaminated Proteins

Unless otherwise specified the data below make specific reference to annexin V, which is referred to as annexin but applies to other proteins specified in this application. The samples of annexin V possess the natural sequence.

Reaction Between Protein and PLP to Produce the Transaminated Proteins, N-Terminal Aldoamide or Ketoamides.

Protein (concentration varied from a few µg/ml to a few mg/ml) was incubated with 10 mM PLP, in 25 mM PBS, pH 6.5, at 37° C. for a specified time. For annexin, the incubation time for high conversion is 4 hr. For leptin, or myoglobin (following Gilmore et al.), the incubation time required is 16 hr.

After the incubation, the sample was subject to centrifuge filtration to remove excess PLP from solution.

Annexin V-ketoamide is not easily distinguished from parent annexin V, since the molecular weight of the two species differ by one mass unit. However, aminoxy substrates, which form oximes with carbonyl species can be used to distinguish the keto-amide from parent.

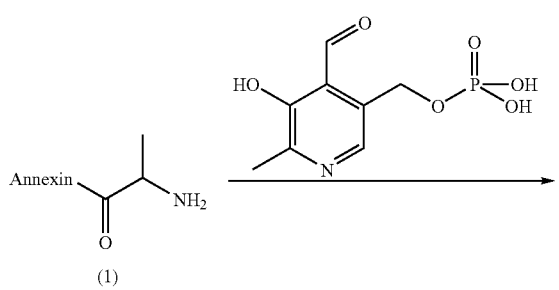

(1)

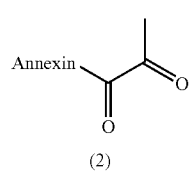

(2)

Reaction Between Annexin V Ketoamide (2) and NOTA Aminooxy Substrate (6).

Annexin ketoamide (2) was incubated with 100 mM NOTA aminooxy substrate (6) at room temperature for 16 hr at pH 6.5 in 25 mM PBS while the reaction mixture was constantly shaken. After the incubation, the sample was subjected to centrifuge filtration to remove excess NOTA aminooxy compound from the solution.

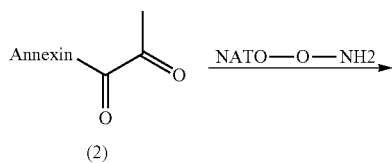

(2)

(3)

The peak at ~35,803 is displaced to 36,175, the sum of NOTA plus the keto-amide, minus water, consistent with the formation of the oxime (3).

As a control, annexin V, untreated with PLP, did not give a discernible product when incubated with the NOTA aminooxy substrate (3) under the same conditions as above.

Reaction Between Protein Aldoamide/Ketoamide with Bis-Aminooxy Compounds to Make Protein Aminooxy Product Protein aldoamide/ketoamide was incubated with 100 mM bis-aminooxy compound (n=4-8) at room temp for 4 to 16 hr and the reaction mixture was constantly shaken. After the reaction, the sample was subject to centrifuge filtration to remove the excess bis-aminooxy compound from solution. The aminoxy-oxime (4) was obtained.

(2)

(4)

Reaction Between Aminoxyprotein (4) and 4-Fluorobenzaldehyde.

Aminoxy-annexin (4), obtained as described above, was incubated with 1 mM 4-fluorobenzaldehyde at room temp for 10 min, at pH 6.5 in 25 mM PBS. The reaction is essentially complete within 10 min to give the corresponding oxime (5). The presence of aniline accelerates the reaction. The reaction mixture was then subjected to centrifuge filtration to remove excess 4-fluorobenzaldehyde from solution.

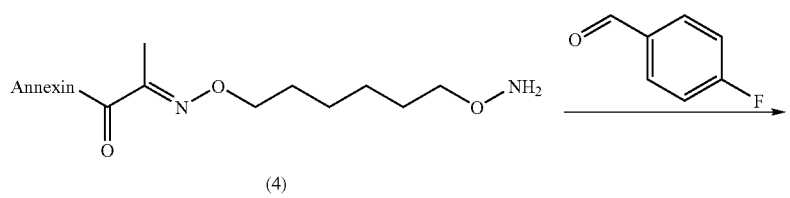

(4)

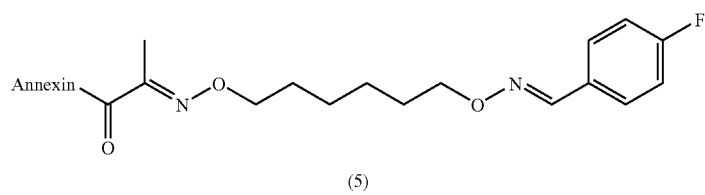

(5)

Reaction Between Aminoxy-Proteins and Exemplary Di-Aldehyde or Tri-Aldehyde Compounds to Introduce Aldehyde Functions onto the Protein Framework Aminoxy annexin V oxime (4) was incubated with 1 mM polyaldehyde compounds (exemplified by terephthaldehyde, isophthaldehyde, 2,6-diformylpyridine and 1,3,5-triformylbenzene at room temp for 10 min (buffer, pH). The reaction to form the mono-aldoxime with the protein species is complete within 10 min. Only one of the two or three aldehyde groups of the polyaldehyde substrates is consumed. This phenomenology is a consequence of the much lower rates of competing reactions: reaction of aminoxyproteins with newly formed aldehyde-proteins and the reaction of protein nucleophiles and aldehydes at pH 6.5. The presence of aniline can further accelerate the rate. The reaction mixture was then subject to centrifuge filtration to remove excess di-aldehyde or tri-aldehyde starting material. This procedure thus constitutes a method for introducing aldehydes onto a protein framework enabling further modification, and reverses the polarity of the protein for organic chemical reactivity.

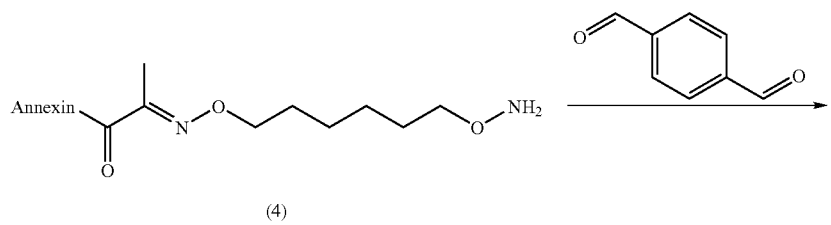

(4)

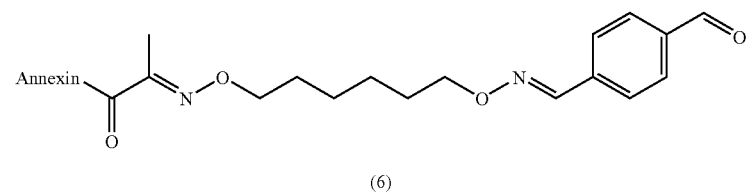

(6)

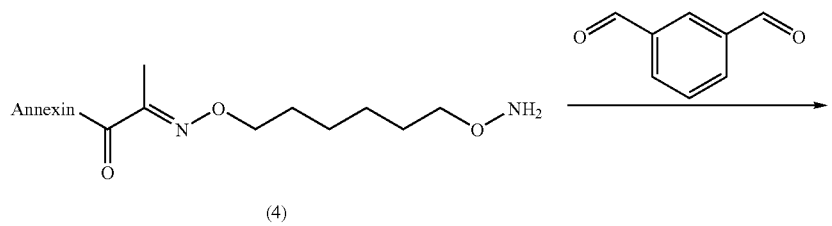

(4)

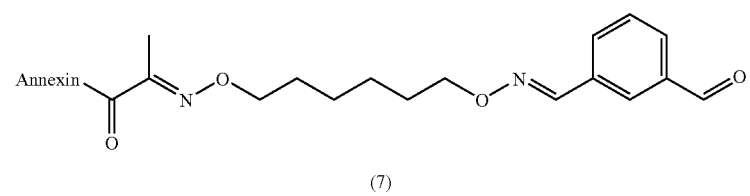

(7)

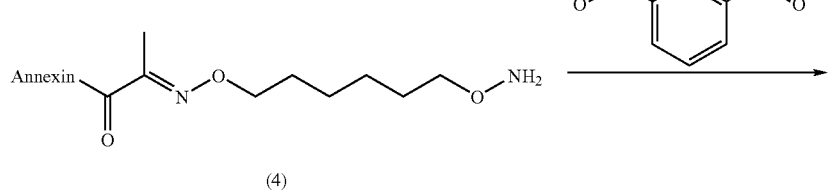

(4)

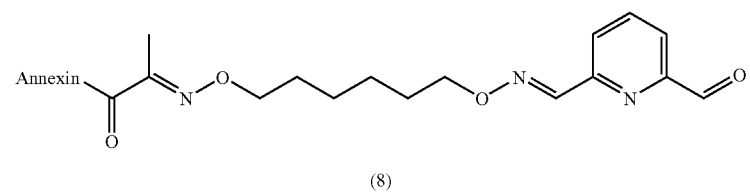

(8)

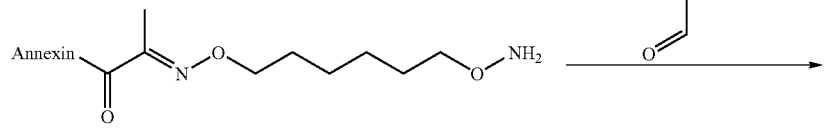

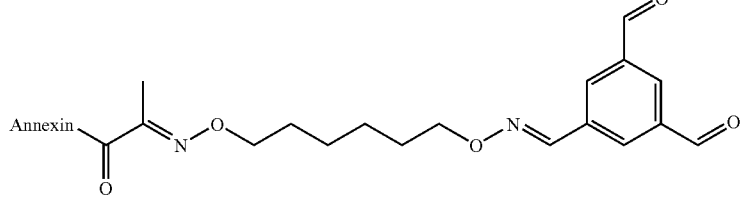

Reaction Between Protein-Aldehydes (7) and Aminooxy Substrates.

Protein aldehyde (7) or protein di-aldehyde (9) as described above were incubated with 1 mM aminooxy substrates at room temp, pH 6.5, in 25 mM PBS with or without 50 mM aniline. In the absence of aniline or ethylene diamine, the reaction takes 1-2 hr to reach completion, whereas in the presence of aniline or ethylene diamine, the reaction is complete within 10 min. The final product from the reaction can be purified by centrifuge filtration.

Figure 2:
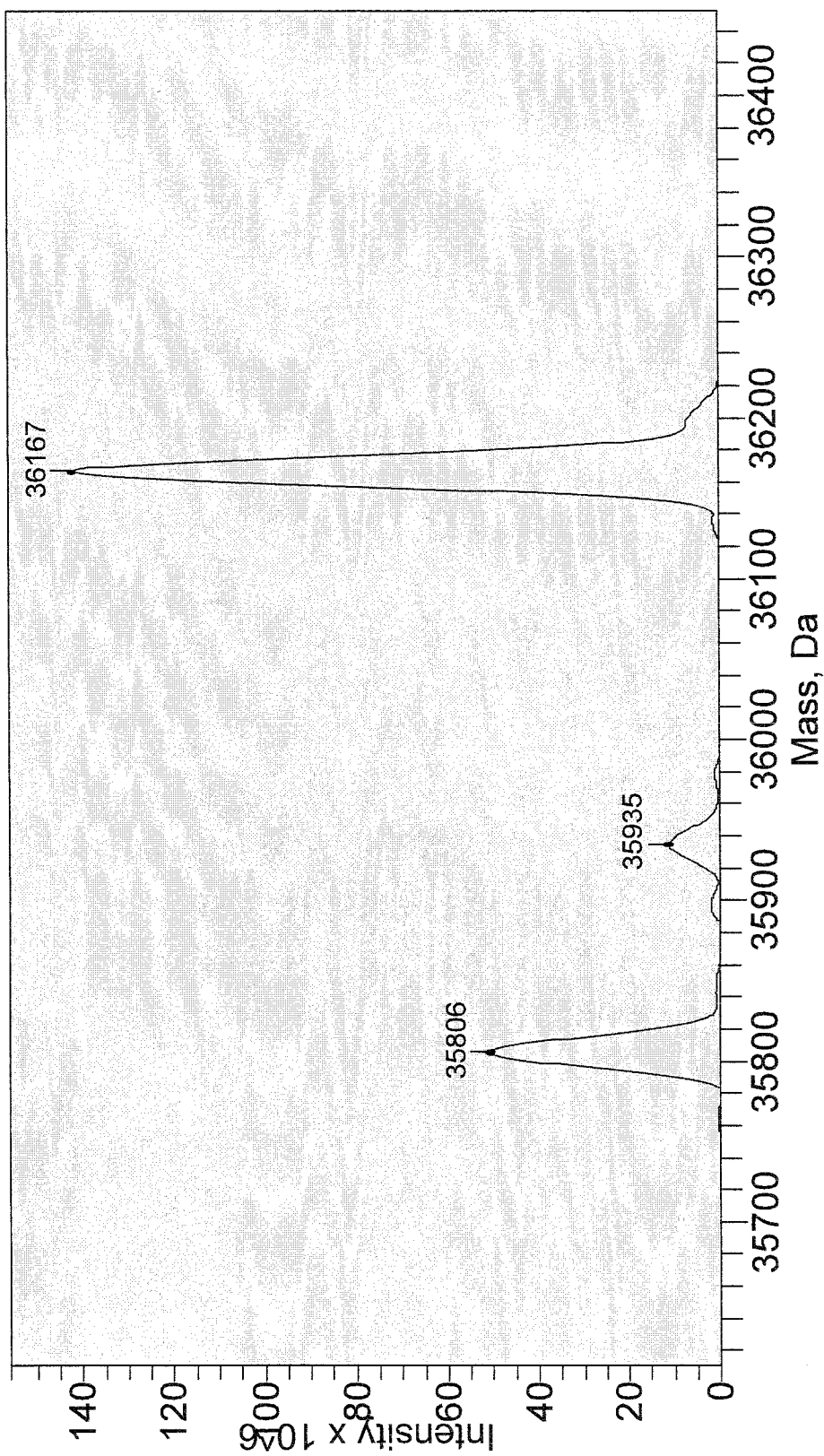
Figure 3:
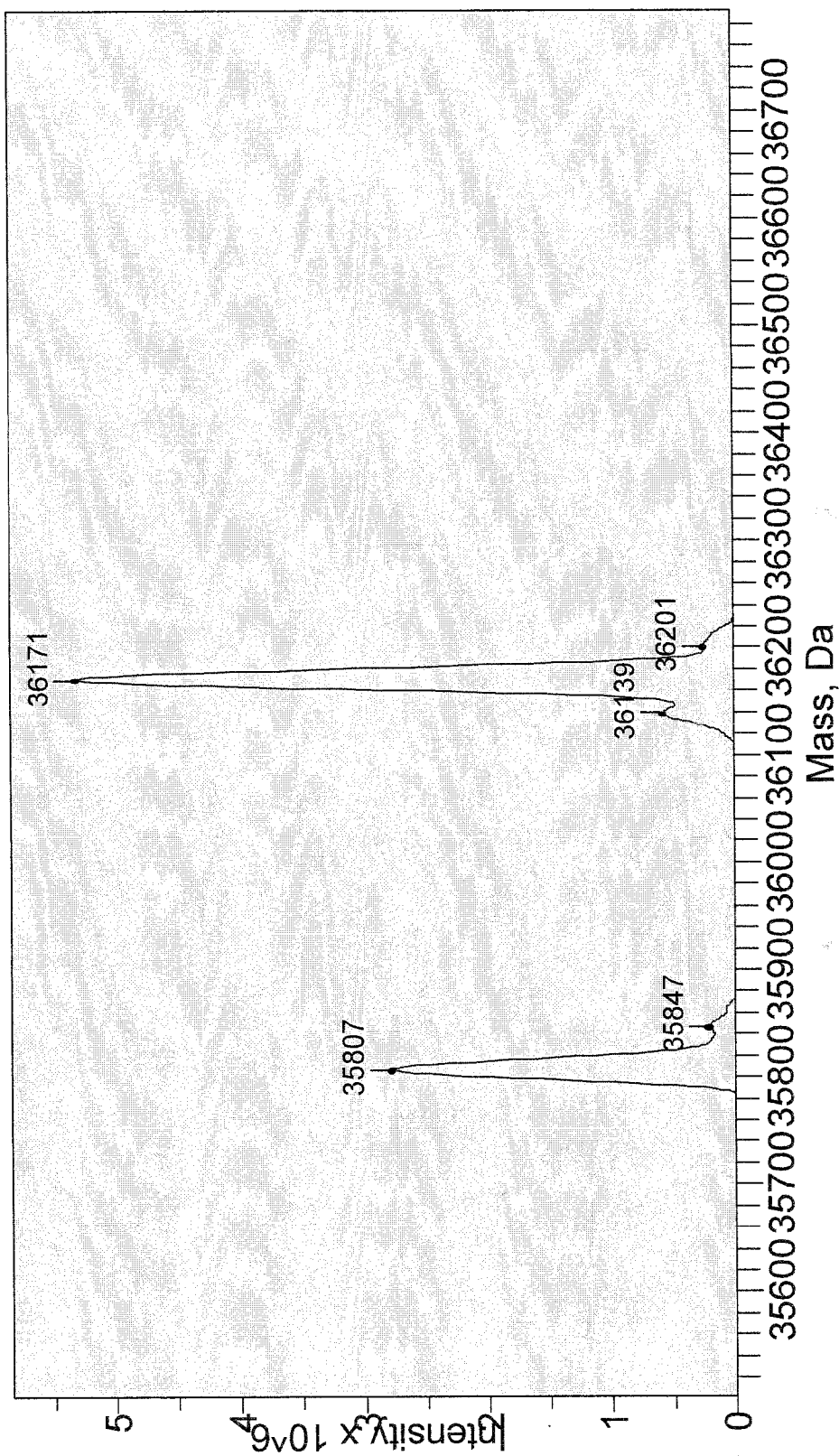

FIGS. 1, 2 and 3 show a mass spectral image depicting the conversion of protein aldehyde 7 to the corresponding site-specific N-terminal modified protein.

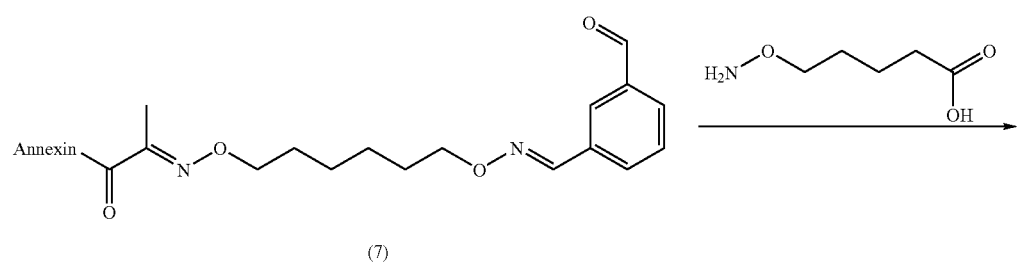

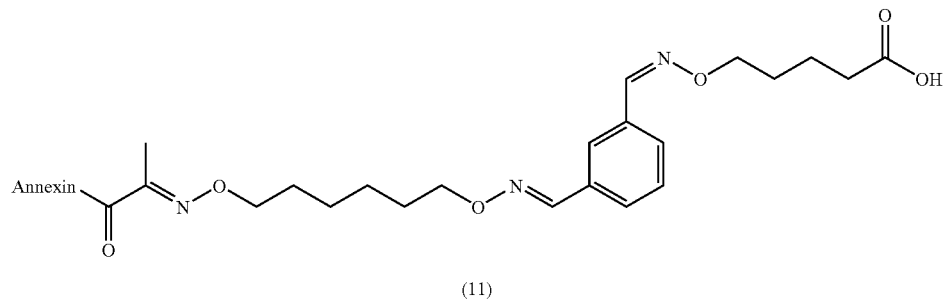

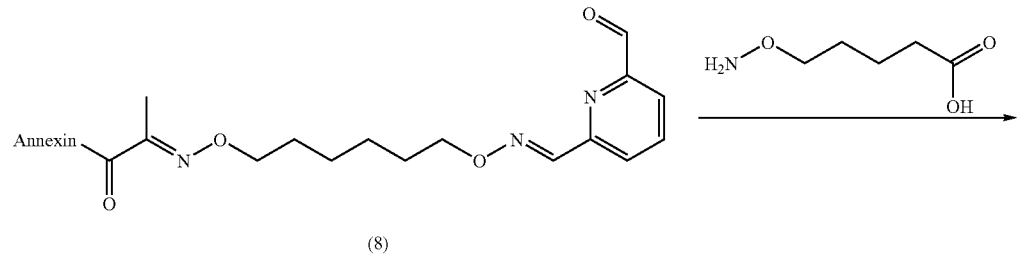

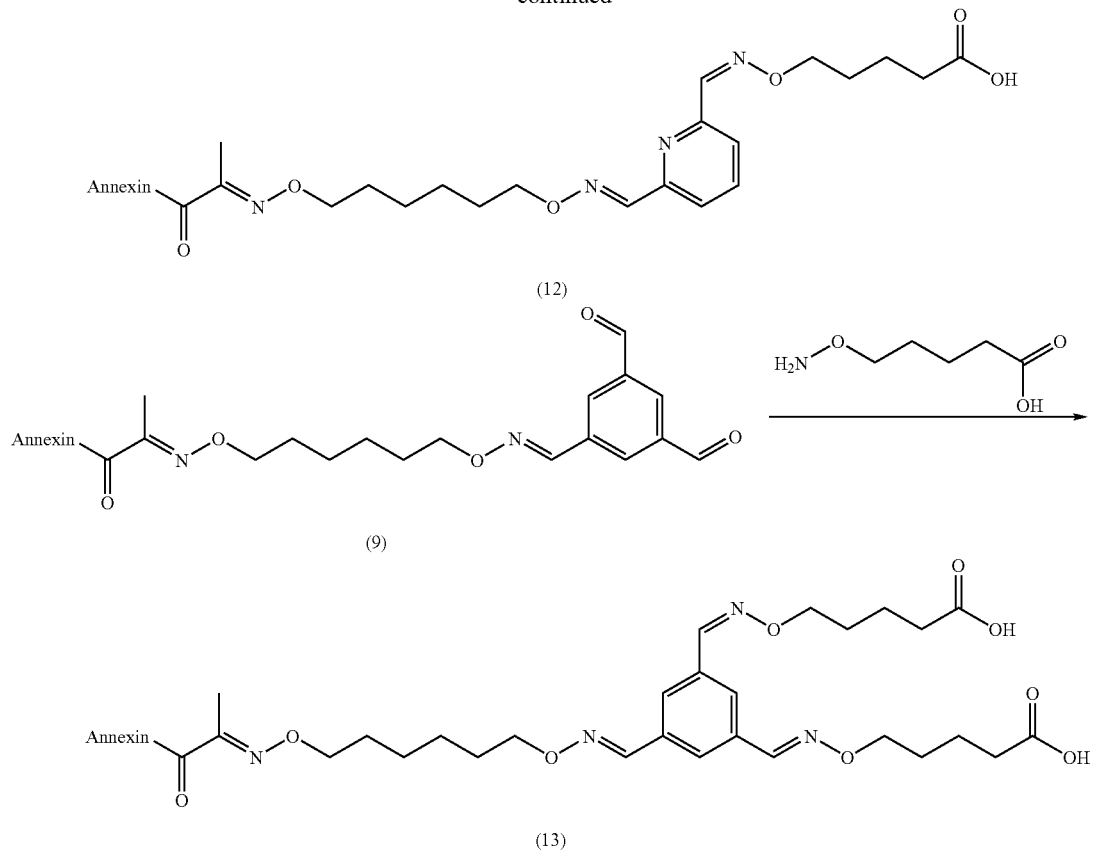

Reaction Between Aminoxy-Proteins (14) and Protein-Aldehydes (6)

Proteins can be coupled together using the aldehyde-aminoxy coupling procedure. For purposes of illustration and the ease of tracking the combined masses of the coupled proteins myoglobin was used as a component. Either protein of the pair can serve as the donor nucleophile or acceptor aldehyde to generate heterodimers. Myoglobin-aldehyde (14, prepared analogously to (4)) and annexin-aldehyde (6) was mixed in a molar ratio of 1 to 1. The mixture was incubated at room temp for 16 hr, with or without the presence of 50 mM aniline and the mixture was constantly shaken. The scheme below illustrates the presence of the expected mass of the conjugate along with the reactive forms of the proteins. The presence of aniline accelerates the reaction and thus leads to higher yields.

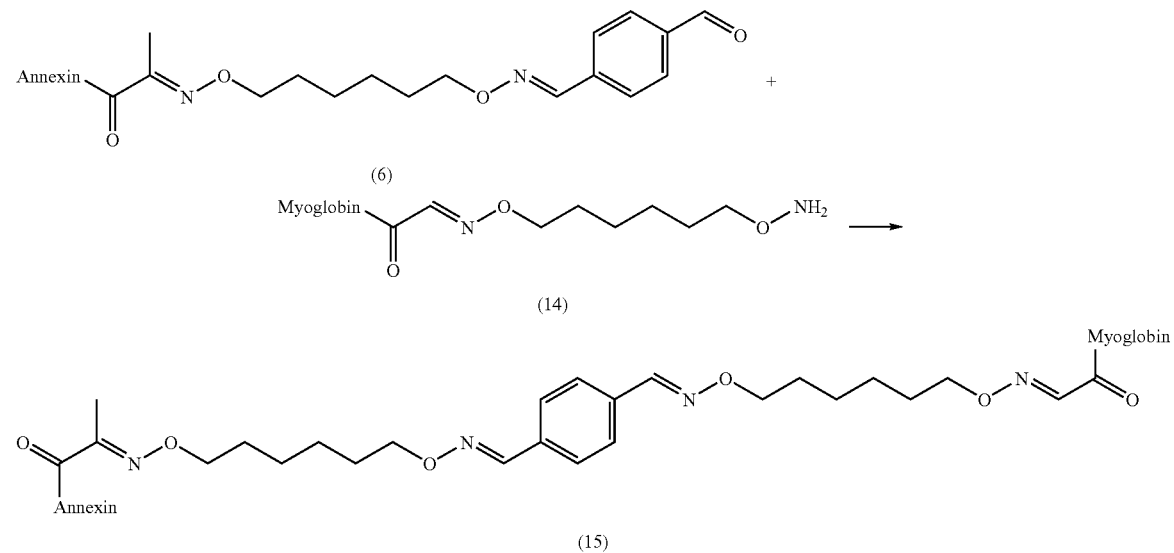

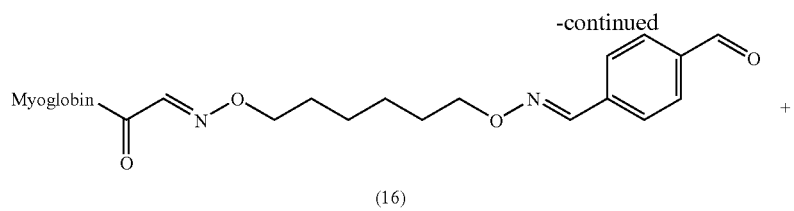
(16)
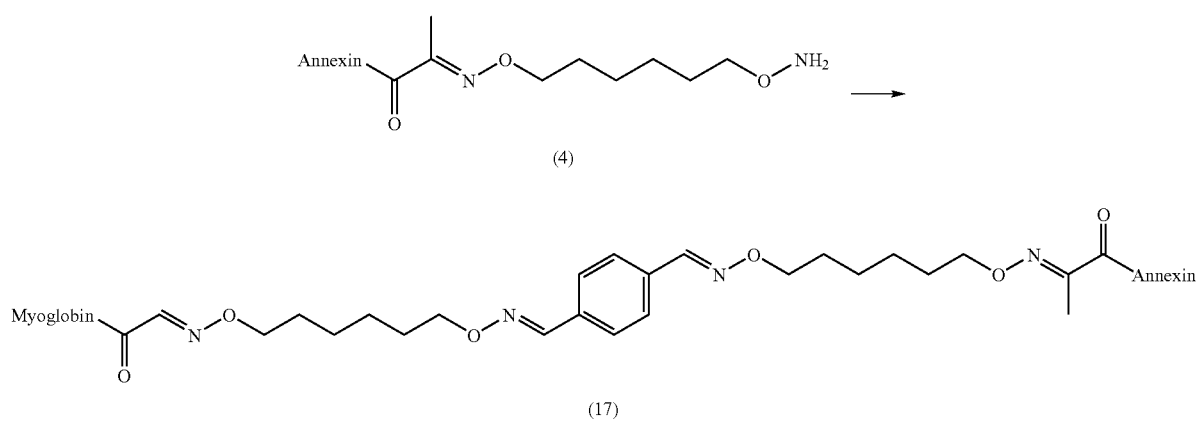
Leptin
Following the precedents of annexin V, above the ketoamide of leptin has been obtained in high conversion, illustrated by the formation of oxime (21) of requisite mass from the coupling of (20) and 4-aminoxypentanoic acid.
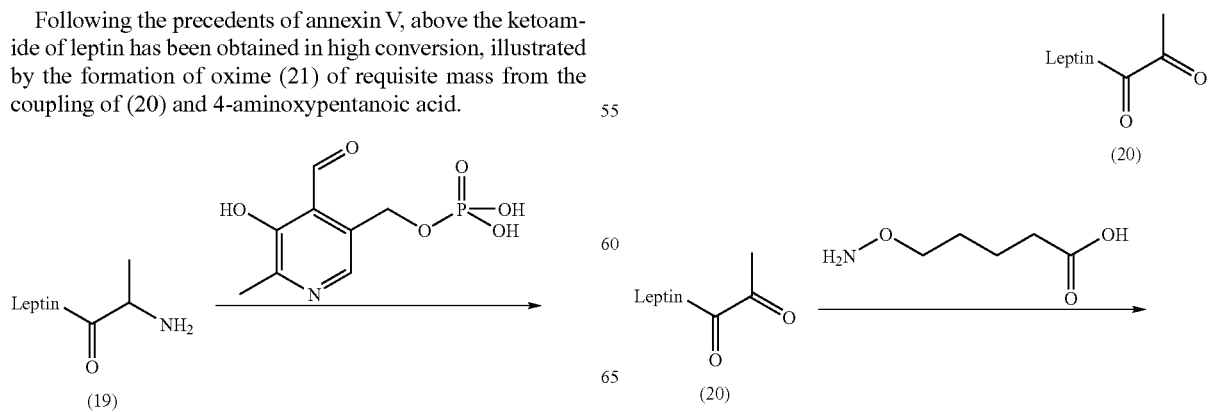

-continued

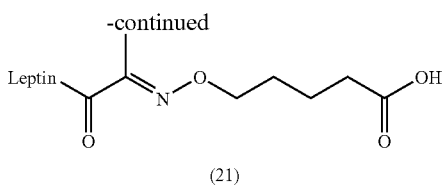

(21)

A skilled artisan appreciates that chemical modifications such as those involving a functional group transformation of an amino group to the corresponding oxime derivative is generally unstable because it can undergo a facile reversible conversion back to the amine. However, as evidenced by the above examples and supporting spectral data, a variety of stable adducts can be obtained. In particular, some of the adducts can be obtained in nearly quantitative yield. An advantage of the present invention is that a series of transformations can be carried out in a multi-step fashion in fairly short duration of time and amenable reaction conditions. Another advantage of the present invention is the stability of the adducts obtained. Yet another advantage of the present invention is the ability of the stable adducts to undergo further chemical transformations. Yet another advantage of the present invention is the robustness of the multi-step synthetic process to obtain a variety of stable adducts in high yields.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein can be utilized according to such related embodiments of the present invention. Thus, the following claims are intended to encompass within their scope modifications, substitutions, and variations to processes, manufactures, compositions of matter, compounds, means, methods, and/or steps disclosed herein.

The contents of any patents, patent applications, and references cited throughout the specification are herein incorporated by reference in their entireties.

The invention claimed is:

1. A compound of the formula:

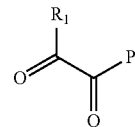

wherein,

P is a protein selected from the group consisting of granulocyte macrophage colony-stimulating factor, human superoxide dismutase, an annexin protein and leptin, wherein P is directly modified at the N-terminus, and R1 is selected from the group consisting of hydrogen, methyl and α-amino acid side chain.

2. The compound of claim 1 wherein P is an annexin protein.

3. The compound of claim 1 wherein P is an annexin V protein.

\* \* \* \* \*